United States Patent
Budiman et al.

(10) Patent No.: US 9,462,970 B2
(45) Date of Patent: Oct. 11, 2016

(54) METHODS OF LAG-COMPENSATION FOR ANALYTE MEASUREMENTS, AND DEVICES RELATED THERETO

(71) Applicant: Abbott Diabetes Care Inc., Alameda, CA (US)

(72) Inventors: Erwin S. Budiman, Fremont, CA (US); David L. Li, Fullerton, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 562 days.

(21) Appl. No.: 13/869,813

(22) Filed: Apr. 24, 2013

(65) Prior Publication Data

US 2013/0304389 A1   Nov. 14, 2013

Related U.S. Application Data

(60) Provisional application No. 61/637,748, filed on Apr. 24, 2012.

(51) Int. Cl.
| | |
|---|---|
| *G01N 33/48* | (2006.01) |
| *G01N 31/00* | (2006.01) |
| *G06G 7/48* | (2006.01) |
| *G06G 7/58* | (2006.01) |
| *A61B 5/145* | (2006.01) |

(52) U.S. Cl.
  CPC .................................. *A61B 5/14532* (2013.01)

(58) Field of Classification Search
  None
  See application file for complete search history.

(56) References Cited

U.S. PATENT DOCUMENTS

| | | |
|---|---|---|
| 4,545,382 A | 10/1985 | Higgins et al. |
| 4,711,245 A | 12/1987 | Higgins et al. |
| 5,262,035 A | 11/1993 | Gregg et al. |
| 5,262,305 A | 11/1993 | Heller et al. |
| 5,264,104 A | 11/1993 | Gregg et al. |
| 5,320,725 A | 6/1994 | Gregg et al. |
| 5,356,786 A | 10/1994 | Heller et al. |
| 5,509,410 A | 4/1996 | Hill et al. |
| 5,593,852 A | 1/1997 | Heller et al. |
| 5,601,435 A | 2/1997 | Quy |
| 5,628,890 A | 5/1997 | Carter et al. |
| 5,820,551 A | 10/1998 | Hill et al. |
| 5,822,715 A | 10/1998 | Worthington et al. |
| 5,899,855 A | 5/1999 | Brown |
| 5,918,603 A | 7/1999 | Brown |

(Continued)

FOREIGN PATENT DOCUMENTS

| | | | |
|---|---|---|---|
| WO | WO 2005/041766 | * | 5/2005 |
| WO | WO 2008/088490 | * | 7/2008 |

(Continued)

*Primary Examiner* — Larry D Riggs, II
(74) *Attorney, Agent, or Firm* — Edward J. Baba; Khin K. Chin; Bozicevic, Field & Francis LLP

(57) ABSTRACT

In some aspects, methods of lag compensation of analyte measurements are provided. Methods of lag-compensation are provided for analyte point measurements and/or for analyte rate-of-change measurements. The methods include receiving a series of uncompensated analyte measurements and determining parameter values for analyte point and/or rate-of-change estimates based on reference analyte measurements. The analyte rate-of-change estimate is based on a sum of a plurality of scaled rates-of-changes. The analyte point estimate is based on a sum of an analyte point and a sum of a plurality of scaled rates-of-changes. Devices related to the methods are also provided.

62 Claims, 15 Drawing Sheets

(56) References Cited

U.S. PATENT DOCUMENTS

| | | |
|---|---|---|
| 6,071,391 A | 6/2000 | Gotoh et al. |
| 6,121,009 A | 9/2000 | Heller et al. |
| 6,134,461 A | 10/2000 | Say et al. |
| 6,144,837 A | 11/2000 | Quy |
| 6,161,095 A | 12/2000 | Brown |
| 6,175,752 B1 | 1/2001 | Say et al. |
| 6,270,455 B1 | 8/2001 | Brown |
| 6,284,478 B1 | 9/2001 | Heller et al. |
| 6,377,894 B1 | 4/2002 | Deweese et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,579,690 B1 | 6/2003 | Bonnecaze et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,654,625 B1 | 11/2003 | Say et al. |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,764,581 B1 | 7/2004 | Forrow et al. |
| 6,881,551 B2 | 4/2005 | Heller et al. |
| 6,893,545 B2 | 5/2005 | Gotoh et al. |
| 6,932,894 B2 | 8/2005 | Mao et al. |
| 7,090,756 B2 | 8/2006 | Mao et al. |
| 7,167,818 B2 | 1/2007 | Brown |
| 7,299,082 B2 | 11/2007 | Feldman et al. |
| 7,811,231 B2 | 10/2010 | Jin et al. |
| 7,822,557 B2 | 10/2010 | Chen et al. |
| 8,103,471 B2 | 1/2012 | Hayter |
| 8,106,780 B2 | 1/2012 | Goodnow et al. |
| 2007/0095661 A1 | 5/2007 | Wang et al. |
| 2008/0177164 A1 | 7/2008 | Heller et al. |
| 2008/0179187 A1 | 7/2008 | Ouyang et al. |
| 2009/0192380 A1* | 7/2009 | Shariati ............... A61B 5/7475 600/365 |
| 2009/0198118 A1* | 8/2009 | Hayter ............... A61B 5/14532 600/347 |
| 2010/0198034 A1 | 8/2010 | Thomas et al. |
| 2010/0213057 A1 | 8/2010 | Feldman et al. |
| 2010/0324392 A1 | 12/2010 | Yee et al. |
| 2010/0326842 A1 | 12/2010 | Mazza et al. |
| 2011/0120865 A1 | 5/2011 | Bommakanti et al. |
| 2011/0124993 A1 | 5/2011 | Bommakanti et al. |
| 2011/0124994 A1 | 5/2011 | Bommakanti et al. |
| 2011/0126188 A1 | 5/2011 | Bernstein et al. |
| 2011/0193704 A1 | 8/2011 | Harper et al. |
| 2011/0213225 A1 | 9/2011 | Bernstein et al. |
| 2011/0256024 A1 | 10/2011 | Cole et al. |
| 2011/0257495 A1 | 10/2011 | Hoss et al. |
| 2011/0270062 A1* | 11/2011 | Goode |
| 2012/0157801 A1 | 6/2012 | Hoss et al. |
| 2012/0245447 A1 | 9/2012 | Karan et al. |
| 2012/0323098 A1 | 12/2012 | Moein et al. |

FOREIGN PATENT DOCUMENTS

| | | | |
|---|---|---|---|
| WO | WO 2010/039744 | * | 4/2010 |
| WO | WO 2010/077328 | * | 7/2010 |

* cited by examiner

METHODS OF LAG-COMPENSATION FOR ANALYTE MEASUREMENTS, AND DEVICES RELATED THERETO

CROSS-REFERENCE TO RELATED APPLICATION

This application claims the benefit of priority under 35 U.S.C. §119(e) to U.S. Provisional Patent Application No. 61/637,748 filed Apr. 24, 2012, the disclosure of which is incorporated by reference herein in its entirety.

INTRODUCTION

In many instances it is desirable or necessary to regularly monitor the concentration of particular constituents in a fluid. A number of systems are available that analyze the constituents of bodily fluids such as blood, urine and saliva. Examples of such systems conveniently monitor the level of particular medically significant fluid constituents, such as, for example, cholesterol, ketones, vitamins, proteins, and various metabolites or blood sugars, such as glucose. Diagnosis and management of patients suffering from diabetes mellitus, a disorder of the pancreas where insufficient production of insulin prevents normal regulation of blood sugar levels, requires carefully monitoring of blood glucose levels on a daily basis. A number of systems that allow individuals to easily monitor their blood glucose are currently available. Some of these systems include electrochemical biosensors, including those that comprise a glucose sensor that is adapted for complete or partial insertion into a subcutaneous site within the body for the continuous or periodic (e.g., on-demand) in vivo monitoring of glucose levels in bodily fluid (e.g., blood or interstitial fluid (ISF)) of the subcutaneous site. ISF glucose lags in time behind blood glucose. That is, if the blood glucose is falling and reaches a low point, the ISF glucose will reach that low point some time later, such as 10 minutes for example. Traditionally, the goal of analyte monitoring systems is to provide results that approximate blood glucose concentrations since blood glucose concentrations better represent the glucose level in the patient's blood.

SUMMARY

In some aspects of the present disclosure, methods of lag compensation for analyte point measurements are provided. The methods include receiving a series of uncompensated analyte measurements; and determining a first set of parameter values for an analyte point estimate based on reference analyte measurements. The analyte point estimate is based on a sum of an analyte point and a sum of a plurality of scaled rates-of-changes. The analyte point corresponds to measurements at an initial reference time. The rates-of-changes include a first rate-of-change from the initial reference time to a first prior reference time, and a second rate-of-change from the initial reference time to a second prior reference time.

In some aspects of the present disclosure, methods of lag compensation for analyte rate-of-change measurements are provided. The methods include receiving reference analyte measurements, and determining a first set of parameter values for an analyte rate-of-change estimate based on the reference analyte measurements. The analyte rate-of-change estimate is based on a sum of a plurality of scaled rates-of-changes. The rates-of-changes include a first rate-of-change from an initial reference time to a first prior reference time, and a second rate-of-change from the initial reference time to a second prior reference time.

In some aspects of the present disclosure, methods of lag compensation for analyte point measurements and analyte rate-of-change measurements are provided. The methods include receiving reference analyte measurements, and determining a first set of parameter values for an analyte point estimate based on the reference analyte measurements. The analyte point estimate is based on a sum of an analyte point and a sum of a first plurality of scaled rates-of-changes. The analyte point corresponds to measurements at an initial reference time. The rates-of-changes of the first plurality include a first rate-of-change from the initial reference time to a first prior reference time, and a second rate-of-change from the initial reference time to a second prior reference time. The methods also include determining a second set of parameter values for an analyte rate-of-change estimate based on the reference analyte measurements. The analyte rate-of-change estimate is based on the sum of a second plurality of scaled rates-of-changes. The rates-of-changes of the second plurality include a third rate-of-change from an initial reference time to a third prior reference time, and a fourth rate-of-change from the initial reference time to a fourth prior reference time.

In some aspects of the present disclosure, articles of manufacture for lag compensation of analyte point measurements are provided. The articles of manufacture include a machine-readable medium having machine-executable instructions stored thereon for lag compensation of analyte measurements. The instructions include instructions for receiving reference analyte measurements, and instructions for determining a first set of parameter values for an analyte point estimate based on the reference analyte measurements. The analyte point estimate is based on a sum of an analyte point and a sum of a plurality of scaled rates-of-changes. The analyte point corresponds to measurements at an initial reference time. The rates-of-changes include a first rate-of-change from the initial reference time to a first prior reference time, and a second rate-of-change from the initial reference time to a second prior reference time.

In some aspects of the present disclosure, articles of manufacture for lag compensation of analyte rate-of-change measurements are provided. The articles of manufacture include a machine-readable medium having machine-executable instructions stored thereon for lag compensation of analyte measurements. The instructions include instructions for receiving reference analyte measurements, and instructions for determining a first set of parameter values for an analyte rate-of-change estimate based on the reference analyte measurements. The analyte rate-of-change estimate is based on a sum of a plurality of scaled rates-of-changes. The rates-of-changes include a first rate-of-change from an initial reference time to a first prior reference time, and a second rate-of-change from the initial reference time to a second prior reference time.

In some aspects of the present disclosure, articles of manufacture for lag compensation of analyte point measurements and analyte rate-of-change measurements are provided. The articles of manufacture include a machine-readable medium having machine-executable instructions stored thereon for lag compensation of analyte measurements. The instructions include instructions for receiving reference analyte measurements, and instructions for determining a first set of parameter values for an analyte point estimate based on the reference analyte measurements. The analyte point estimate is based on a sum of an analyte point and a sum of a first plurality of scaled rates-of-changes. The analyte point corresponds to measurements at an initial reference time. The rates-of-changes of the first plurality include a first rate-of-change from the initial reference time to a first prior reference time and a second rate-of-change from the initial reference time to a second prior reference time. The articles of manufacture also include instructions for determining a second set of parameter values for an analyte rate-of-change estimate based on the reference analyte measurements. The analyte rate-of-change estimate is based on the sum of a second plurality of scaled rates-of-changes. The rates-of-changes of the second plurality include a third rate-of-change from an initial reference time to a third prior reference time, and a fourth rate-of-change from the initial reference time to a fourth prior reference time.

INCORPORATION BY REFERENCE

Additional embodiments of analyte monitoring systems suitable for practicing methods of the present disclosure are described in U.S. Pat. Nos. 6,175,752; 6,134,461; 6,579,690; 6,605,200; 6,605,201; 6,654,625; 6,746,582; 6,932,894; 7,090,756; 5,356,786; 6,560,471; 5,262,035; 6,881,551; 6,121,009; 7,167,818; 6,270,455; 6,161,095; 5,918,603; 6,144,837; 5,601,435; 5,822,715; 5,899,855; 6,071,391; 6,377,894; 6,600,997; 6,514,460; 5,628,890; 5,820,551; 6,736,957; 4,545,382; 4,711,245; 5,509,410; 6,540,891; 6,730,200; 6,764,581; 6,503,381; 6,676,816; 6,893,545; 6,514,718; 5,262,305; 5,593,852; 6,746,582; 6,284,478; 7,299,082; 7,811,231; 7,822,557; 8,106,780; 8,103,471; U.S. Patent Application Publication No. 2010/0198034; U.S. Patent Application Publication No. 2010/0324392; U.S. Patent Application Publication No. 2010/0326842 U.S. Patent Application Publication No. 2007/0095661; U.S. Patent Application Publication No. 2008/0179187; U.S. Patent Application Publication No. 2008/0177164; U.S. Patent Application Publication No. 2011/0120865; U.S. Patent Application Publication No. 2011/0124994; U.S. Patent Application Publication No. 2011/0124993; U.S. Patent Application Publication No. 2010/0213057; U.S. Patent Application Publication No. 2011/0213225; U.S. Patent Application Publication No. 2011/0126188; U.S. Patent Application Publication No. 2011/0256024; U.S. Patent Application Publication No. 2011/0257495; U.S. Patent Application Publication No. 2012/0157801; U.S. Patent Application Publication No. 2012/024544; U.S. Patent Application Publication No. 2012/0323098; U.S. Patent Application Publication No. 2012/0157801; U.S. Patent Application Publication No. 2010/0213057; U.S. Patent Application Publication No. 2011/0193704; U.S. Provisional Patent Application No. 61/582,209; and U.S. Provisional Patent Application Publication No. 61/581,065; the disclosures of each of which are incorporated herein by reference in their entirety.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol that is used in one drawing to refer to a particular element may be used in another drawing to refer to a like element.

Figure 1:
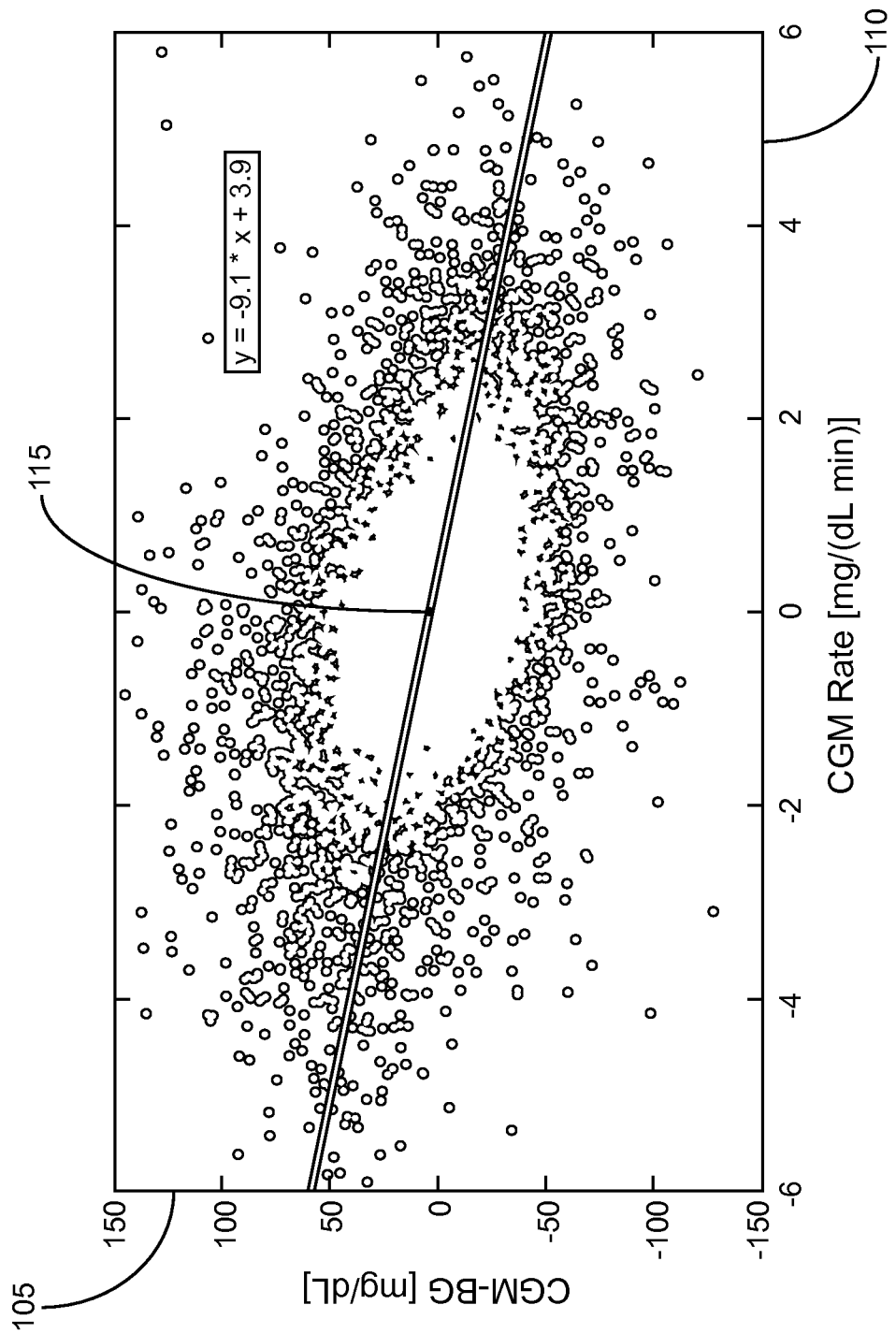
FIG. 1 illustrates an example scatter plot of the difference between sensor glucose (CGM) and blood glucose (BG) versus sensor glucose rate.

Before the embodiments of the present disclosure are described, it is to be understood that the present disclosure is not limited to particular embodiments described, as such may, of course, vary. It is also to be understood that the terminology used herein is for the purpose of describing particular embodiments only, and is not intended to be limiting, since the scope of the embodiments of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the present disclosure. The upper and lower limits of these smaller ranges may independently be included or excluded in the range, and each range where either, neither or both limits are included in the smaller ranges is also encompassed within the present disclosure, subject to any specifically excluded limit in the stated range. Where the stated range includes one or both of the limits, ranges excluding either or both of those included limits are also included in the present disclosure.

In the description of the present disclosure herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the present disclosure. It will be understood that a corresponding description of these various terms applies to corresponding linguistic or grammatical variations or forms of these various terms. It will also be understood that the present disclosure is not limited to the terminology used herein, or the descriptions thereof, for the description of particular embodiments. Merely by way of example, the present disclosure is not limited to particular analytes, bodily or tissue fluids, blood or capillary blood, or sensor constructs or usages, unless implicitly or explicitly understood or stated otherwise, as such may vary. The publications discussed herein are provided solely for their disclosure prior to the filing date of the application. Nothing herein is to be construed as an admission that the embodiments of the present disclosure are not entitled to antedate such publication by virtue of prior invention. Further, the dates of publication provided may be different from the actual publication dates which may need to be independently confirmed.

DETAILED DESCRIPTION

In general, the present disclosure relates to method of providing an analyte estimate, such as a glucose estimate, for a continuous glucose monitoring (CGM) system—e.g., such as the FreeStyle Navigator (FSN) CGM system manufactured by Abbott Diabetes Care Inc. For example, such CGM systems include an analyte sensor that may be fully or partially implanted in the subcutaneous tissue of a subject and coming in contact with and monitoring the analyte level of biological fluid, such as interstitial fluid present in the subcutaneous tissue. In some instances during use, the system may experience a lag between the interstitial fluid-to-blood analyte levels, which may present an artificial source of error for CGM systems. For example, if the blood glucose is falling and reaches a low point, the ISF glucose will reach that low point some time later, such as 10 minutes for example. Therefore, it is desirable to provide results that approximate blood glucose concentrations since blood glucose concentrations better represent the subject's glucose level at any point in time.

In some aspects of the present disclosure, methods are provided that compensate for a lag in glucose level measurements that may be experienced in such systems. This method of lag-compensation is based on the principle that as the rate of change of the glucose level increases, the level of lag in the glucose level in the interstitial fluid to the glucose in the blood will also increase. Accordingly, this method seeks to determine the rate of change of the blood level for two time periods just prior to a reference time and based on the difference in the rate of change for the two time periods will apply a different level of lag correction to the time points. If a first time period has a lower rate of change than a second time period, then the factor of lag compensation applied to the first time period may be lower than the factor of lag compensation applied to the second time period. Based on these scaled rates of change, the glucose measurements are compensated for at the different time points in a relative manner to the determined factor of rate of change.

For example, the methods include receiving a series of uncompensated glucose measurements and determining a first set of parameter values for an glucose level estimate based on reference analyte measurements to compensate for a lag in glucose level measurements. The glucose level estimate is based on a sum of a glucose level and a sum of a plurality of scaled rates-of-changes. The analyte point corresponds to measurements at an initial reference time. The rates-of-changes include a first rate-of-change from the initial reference time to a first prior reference time, and a second rate-of-change from the initial reference time to a second prior reference time. A first set of weighting coefficients are then derived from the first set of parameter values and lag-compensated glucose level measurements are subsequently calculated from the uncompensated glucose measurements by applying the first set of weighting coefficients to corresponding uncompensated analyte measurements received at the initial reference time, the first prior reference time, and the second prior reference time of the first parameter values.

FIG. 1 illustrates an example scatter plot of the difference that may be experienced between sensor glucose (CGM) and blood glucose (BG) versus sensor glucose rate. The difference 105 between the CGM glucose and reference BG measurement (e.g. capillary finger sticks, venous YSI measurements, or other standard or reference measurement) is represented on the vertical axis, while the CGM rate 110 is represented on the horizontal axis. As shown, the discrepancy between the CGM glucose and reference BG changes with respect to the CGM rate. In the example shown, the difference 105 is approximately zero when the CGM rate is zero, as represented by point 115. Thus, when the CGM glucose is not changing, the glucose discrepancy is approximately zero or otherwise minimal. As the CGM rate increases positively, the discrepancy between the CGM glucose and BG increases, with the CGM glucose becoming smaller with respect to the BG, and yielding a negative difference as shown. Similarly, as the CGM rate increases negatively, the discrepancy between the CGM glucose and BG increases, with the CGM glucose becoming larger with respect to the BG, and yielding a positive difference as shown.

Figure 2:
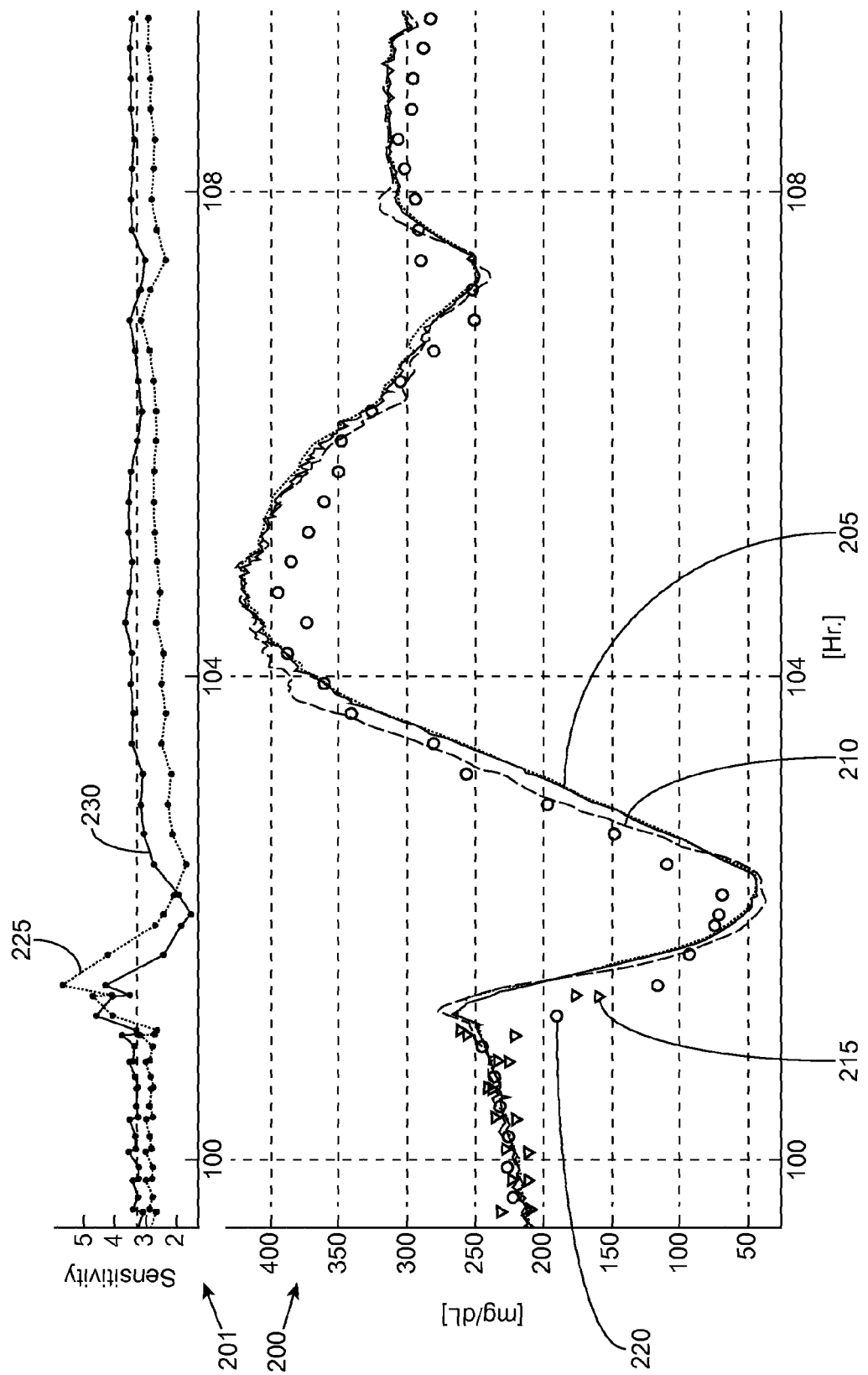
FIG. 2 illustrates graphs of example analyte measurement plots and corresponding calibration factors based on the relationship shown in FIG. 1.

FIG. 2 illustrates graphs of example analyte measurement plots and corresponding calibration factors, called sensitivity, based on the relationship shown in FIG. 1. The bottom sub-graph 200 shows glucose measurement values along the vertical axis (represented in milligrams per deciliter (mg/dL)) and time along the horizontal axis (represented in hours). The sub graph 200 shows uncompensated CGM measurements 205 that has been calibrated to match steady-state reference glucose values, first order lag-compensated measurements 210, and fingerstick reference measurement 215 and YSI reference measurement 220. The top sub-graph illustrates an example computed sensitivity for the uncompensated CGM measurement (0th order model, each value generated by taking the ratio between local CGM and each reference measurement) 225 and an example computed sensitivity for the first order lag-compensated measurement 230 (where each value is generated by taking the first order lag-compensated local CGM and each reference measurement). As rates of change move away from zero, the 0th order model 225 results in a predictable error that persists until rate returns to zero. The 1st order model corrected sensitivity 230 however, remains closer to the true steady-state value except for two regions, where the larger rates of changes exist. The $0^{th}$ order sensitivity 225 is biased slightly lower to facilitate manual comparison against the $1^{st}$ order sensitivity 230.

Figure 3:
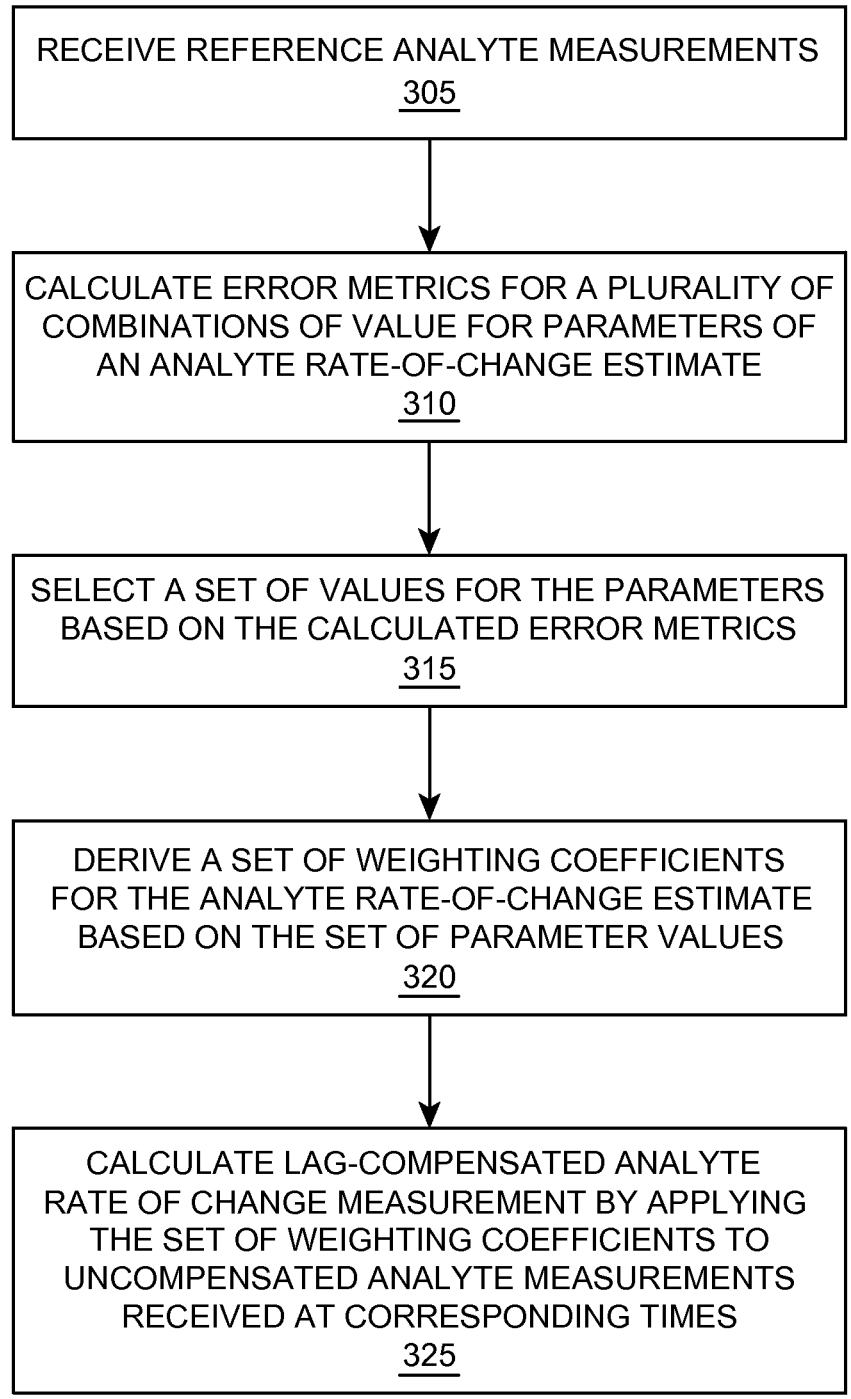
FIG. 3 illustrates flowcharts for a method of lag compensation of analyte rate-of-change measurements, according to one embodiment.
Figure 4:
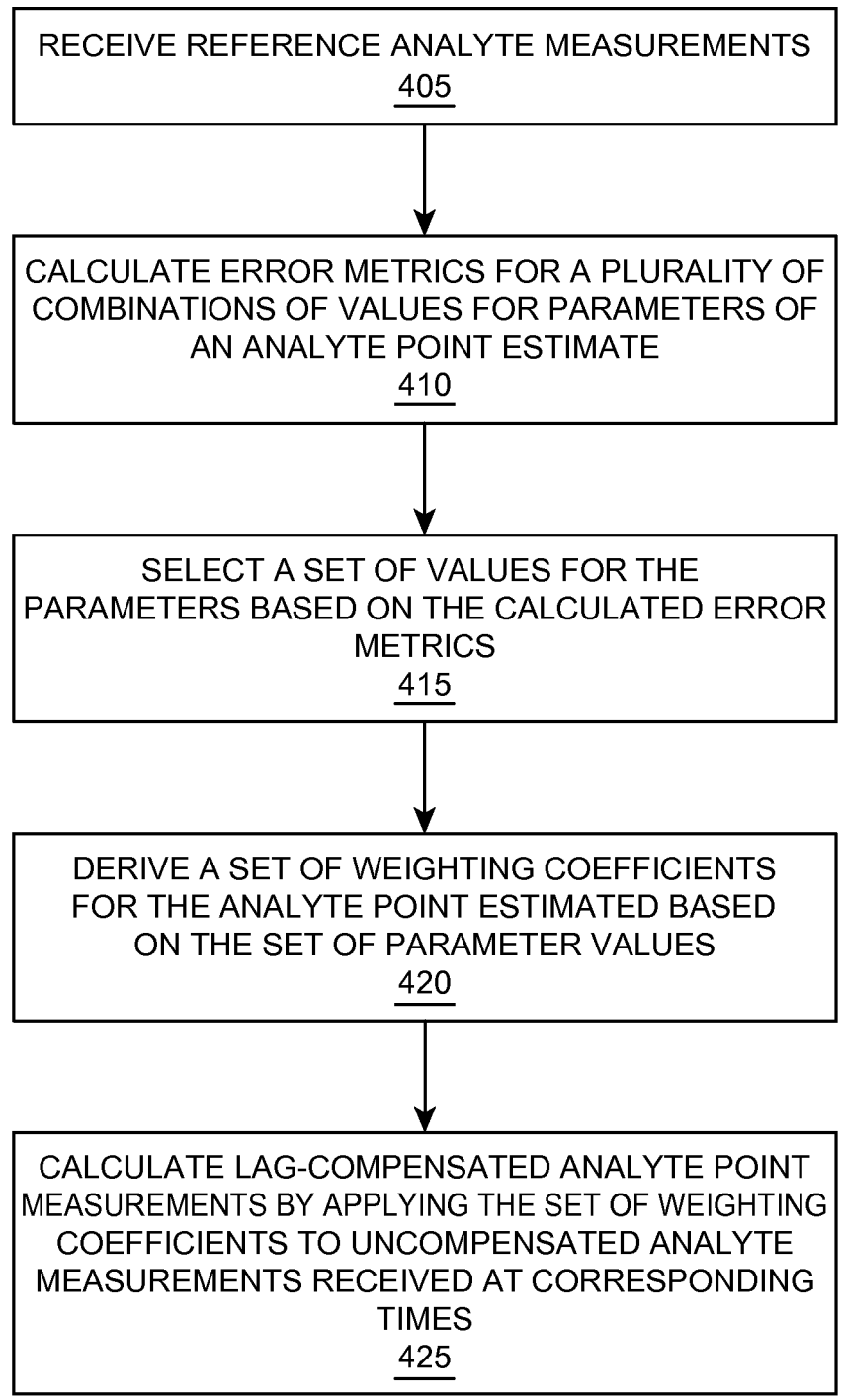
FIG. 4 illustrates flowcharts for a method of lag compensation of analyte point measurements, according to one embodiment.

Exemplary methods according to certain embodiments of lag compensation of analyte rate-of-change measurements and a method of lag compensation of analyte point measurements, are illustrated in FIGS. 3 and 4, respectively. The term "analyte point" is used herein to refer generally to the analyte measurement's magnitude or value. The term "analyte rate-of-change" is used herein to refer generally to the rate at which the analyte measurements are changing. While FIGS. 3 and 4 are described together below, the two methods are independent of one another. In other words, either method may be performed with or without the performance of the other method.

At blocks 305 and 405, reference analyte measurements are received. For example, the reference analyte measurements may be originally derived from a preexisting study and data. This data may contain, for example, a relatively frequent and accurate reference analyte measurements that have been collected over a given time period. Examples of reference analyte measurements include venous glucose measurement using a YSI instrument, or capillary BG measurement using a BG meter.

Referring to FIG. 3, the parameter values for an analyte rate-of-change estimate are determined based on the reference analyte measurements. The analyte rate-of-change estimate is based on a sum of a plurality of scaled rates-of-changes. The rates-of-changes include a rate-of-change from the initial reference time to a first prior reference time, and another rate-of-change from the initial reference time to a second prior reference time that is different than the first prior reference time. It should be appreciated that while two rates-of-changes are described, the analyte rate-of-change estimate may include more than two rates-of-changes, such as three, four, five, or more rates of changes, in other embodiments. The parameter values may include, for example, scalars for each of the rates-of-changes, as well as the prior reference times for each of the rate-of-changes.

For example, in one embodiment, a glucose rate-of-change estimate is represented by a scaled sum of rates-of-changes of CGM values, which may also be referred to herein as a scaled sum of 2 first (backwards) differences of CGM measurements. The glucose rate-of-change estimate may be represented as follows:

$$\hat{G}_b(k) :=$$
$$\frac{c_1}{N_1}[y(k) - y(k-N_1)] + \frac{c_2}{N_2}[y(k) - y(k-N_2)] = \left[\frac{c_1}{N_1} + \frac{c_2}{N_2}\right]y(k) + \left[-\frac{c_1}{N_1}\right]$$

-continued
$$y(k-N_1) + \left[-\frac{c_2}{N_2}\right]y(k-N_2) =$$
$$d_0 y(k) + d_1 y(k-N_1) + d_2 y(k-N_2) - d_0 = d_1 + d_2$$

where k is the sample time index of the sensor data, y is the calibrated sensor measurement, $c_1$ and $c_2$ are scalars, and $N_1$ and $N_2$ are time delay indices. Scalar, $c_1$, is multiplied by a first rate-of-change between two measurements at an $N_1$ time interval apart; and scalar, $c_2$, is multiplied by a second rate-of-change between two measurements at an $N_2$ time interval apart. In this way, two first order components with different time intervals ($N_1$ or $N_2$) between each corresponding raw data pairs (y(k) and y(k-$N_1$) or y(k) and y(k-$N_2$)) may be found and permit the capturing of at least two dominant modes that govern the dynamic lag relationship. As shown, the values of the predetermined, fixed weighting coefficients—$d_0$, $d_1$, and $d_2$—will be based on the values selected for the parameters—$c_1$, $c_2$, $N_1$, $N_2$—of the glucose rate-of-change estimate.

Referring to FIG. 4, the parameter values for the analyte point estimate, such as glucose level estimate, are determined based on the reference analyte measurements. The analyte point estimate is based on a sum of an analyte point and a sum of a plurality of scaled rates-of-changes. The analyte point corresponds to measurements at an initial reference time. The rates-of-changes include a rate-of-change from the initial reference time to a first prior reference time, and another rate-of-change from the initial reference time to a second prior reference time that is different than the first prior reference time. It should be appreciated that while two rates-of-changes are described, the analyte point estimate may include more than two rates-of-changes, such as three, four, five, or more rates of changes. The parameter values may include, for example, scalars for each of the rates-of-changes, as well as the prior reference times for each of the rate-of-changes.

For example, in one embodiment, a glucose point estimate is represented by the following sum of an analyte point and scaled sum of rates-of-changes of CGM values, which may also be referred to herein as a scaled sum of 2 first (backwards) differences of CGM measurements. For instance, the glucose point estimate may be a sum of the latest value plus a sum of 2 scaled first differences. The glucose point estimate may be represented as follows:

$$\hat{G}_b(k) :=$$
$$y(k) + \frac{a_1}{N_1}[y(k) - y(k-N_1)] + \frac{a_2}{N_2}[y(k) - y(k-N_2)] = \left[1 + \frac{a_1}{N_1} + \frac{a_2}{N_2}\right]$$
$$y(k) + \left[-\frac{a_1}{N_1}\right]y(k-N_1) + \left[-\frac{a_2}{N_2}\right]y(k-N_2) =$$
$$b_0 y(k) + b_1 y(k-N_1) + b_2 y(k-N_2)$$

where k is the sample time index of the sensor data, y is the calibrated sensor measurement, $a_1$ and $a_2$ are scalars, and $N_1$ and $N_2$ are time delay indices. Scalar, $a_1$, is multiplied by a first rate-of-change between two measurements at an $N_1$ time interval apart. Scalar, $a_2$, is multiplied by a second rate-of-change between two measurements at an $N_2$ time interval apart. In this way, two first order components with different time intervals ($N_1$ or $N_2$) between each corresponding raw data pairs (y(k) and y(k-$N_1$) or y(k) and y(k-$N_2$)) may be found and permit the capturing of at least two dominant modes that govern the dynamic lag relationship. As shown, the values of the predetermined, fixed weighting coefficients—$b_0$, $b_1$, and $b_2$—will be based on the values selected for the parameters—$a_1$, $a_2$, $N_1$, $N_2$—of the glucose point estimate.

Referring back to FIGS. 1 and 2, while a single 1st order model seems to somewhat reduce the correlation between CGM-to-BG discrepancy and rate in some cases, certain fast excursions demonstrate up to two temporal regions where neither a 0th order nor a $1^{st}$ order model can adequately predict the blood-to-sensor relationship.

In some aspects of the present disclosure, however, accurate predictions of the blood-to-sensor relationship during such fast excursions in the two temporal regions may be provided. With linear time invariant (LTI) models, for example, the transfer function from blood to sensor glucose may be viewed as predominantly first order low pass filter, but there may be one or more near pole-zero cancellations that do not contribute to any measurable sensor signal unless the blood glucose excursion contains the right frequency content. With Finite Impulse Response (FIR) LTI models, for example, taking the sum of more than one (e.g., two as shown in one embodiment) 1st order "rates" may permit similar behavior in that when the blood glucose excursion contains frequency contents that are slower than both "rate" calculations, the output of the model is essentially identical to a single 1st order model. On the other hand, when the blood glucose excursion contains frequency contents that are in between the "bandwidth" of the two components, the output of the embodiments described herein will be different from the single 1st order model. The embodiments described herein provide accurate outputs representing the blood-to-sensor relationship during such fast excursions.

Parameter values may be selected to optimize the analyte point and rate-of-change estimates described for FIGS. 3 and 4. For example, the parameter values for the analyte point and rate-of-change estimates may be determined by calculating error metrics. Similarly, at block 310 of FIG. 3, error metrics are calculated for a plurality of combinations of values as parameters in the analyte rate-of-change estimate. A set of parameter values are then selected based on the calculated error metrics, as represented at block 315.

At block 410 of FIG. 4, error metrics are calculated for a plurality of combinations of values as parameters in the analyte point estimate. A set of parameter values are then selected based on the calculated error metrics, as represented at block 415.

Figure 5:
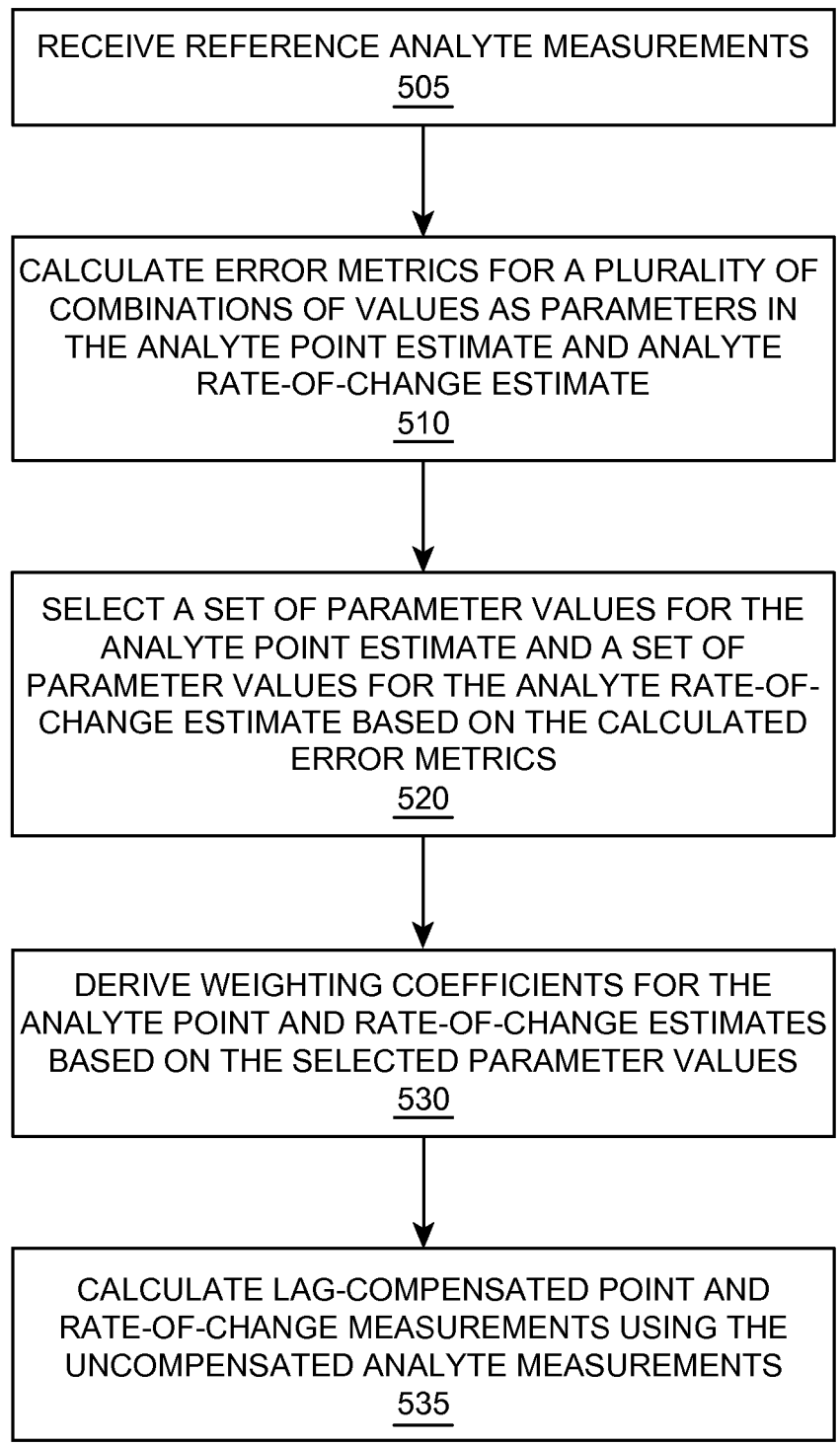
FIG. 5 illustrates a flowchart for a method of lag compensation of analyte point measurements and analyte rate-of-change measurements, according to one embodiment.

The parameter values of the analyte point and rate-of-change estimates may be synthesized using a development set that contains a relatively frequent and accurate reference analyte measurements (e.g., the reference analyte measurements provided in blocks 305 and 405 of FIGS. 4 and 5, respectively). The number of terms in the estimation, as well as the associated delays and coefficients, may be chosen, for example, using the following example method. It should be appreciated that the following optimization example can be performed separately for analyte point and rate-of-change estimates to yield optimized parameters values (e.g., scalars $a_1$, $a_2$; scalars $c_1$, $c_2$; time delays (e.g., $N_1$, $N_2$). It should also be appreciated that while in some embodiments, in-vivo reference glucose from a subject may be enough to perform the entire process described in FIGS. 3 and 4, the preferred embodiment is one where the synthesis is performed offline based on population sensor and reference glucose data, and the final steps 325 and 425 are performed to each patient's in-vivo sensor glucose data. The example optimization method is as follows:

1. Select number of terms in the model (e.g. two terms, with unknown time delays $N_1$ and $N_2$).
2. Define search space of time delays (e.g. $N_1$ in integer increments from 1 to 40 minutes). This encompasses every combination of delays for every term, subject to the constraint ($N_x < N_y$ for $x < y$) (e.g. $N_2$ in integer increments up to 45 minutes, and $N_1 < N_2$).
3. Iterate through search space of delays. For each specific delay combination,
   a. Accumulate all reference data points (e.g. reference glucose readings for point filters or first backwards difference of reference data readings for rate filters)
   b. Accumulate all calibrated sensor data points required to estimate each reference data point. (e.g. $y(k)$, $y(k-N_1)$, $y(k-N_2)$ to estimate the reference value at time k)
   c. Apply an optimization routine (e.g. least squares error (LS) fit, etc.) that determines the coefficients that minimize an error function between the estimated value and the references. It should be appreciated that any variety of optimization routines may be used for the error metric calculation. In one embodiment, using LS fit, coefficients may be chosen that minimize the sum of squared error between the reference glucose value and the estimated glucose value. This would yield the following example cost function which could then be fed into an optimization routine.

$$J := \Sigma (\hat{G}_B - G_B)^2$$

d. Record overall error metric (e.g. Sum of Squared Errors in the case of LS) for this specific delay combination, as well as the resulting optimal scalars (e.g. $a_1$ and $a_2$, or $c_1$ and $c_2$ for each $N_1$ and $N_2$ combination in the search space defined in step 2).
4. Choose the delay combination and its associated coefficients by an external metric. For example, in one embodiment, the combination with the lowest error metric is chosen.

After selecting the parameter values, the weighting coefficients for an estimate may be calculated. For example, weighting coefficients for the analyte rate-of-change estimate may then be derived based on the selected parameter values, as represented at block 320. The weighting coefficients are then implemented in a filter that may be used to calculate lag-compensated rate-of-change estimates using the uncompensated analyte measurements (e.g., sensor glucose measurements), as represented by block 325. For example, the weighting coefficients $d_0$, $d_1$, and $d_2$ (derived based on the values selected for the parameters—$c_1$, $c_2$, $N_1$, $N_2$) may be applied to corresponding data (e.g., uncompensated analyte measurements) received at the initial reference time (e.g., the most recent data available), the first prior reference time $N_1$, and the second prior reference time $N_2$, respectively.

Referring to FIG. 4, weighting coefficients for the analyte point estimate may then be derived based on the selected parameter values, as represented at block 420. The weighting coefficients are then implemented in a filter that may be used to calculate lag-compensated point estimates using the uncompensated analyte measurements (e.g., interstitial glucose measurements), as represented by block 425. For example, the weighting coefficients $b_0$, $b_1$, and $b_2$ (derived based on the values selected for the parameters—$a_1$, $a_2$, $N_1$, $N_2$) may be applied to corresponding data (e.g., uncompensated analyte measurements) received at the initial reference time (e.g., the most recent data available), the first prior reference time $N_1$, and the second prior reference time $N_2$, respectively.

Uncompensated analyte measurements may be received from, for example, interstitial glucose measurements. For instance, a transcutaneously implanted sensor may communicate uncompensated analyte measurements to a data processing device (e.g., analyte monitoring device) implementing the filter. In one embodiment, the implanted sensor is implanted in the subcutaneous tissue and provides uncompensated analyte measurements continuously to an analyte monitoring device (e.g., such as in continuous glucose monitoring (CGM) systems). In another embodiment, the implanted sensor may provide uncompensated analyte measurements intermittently, such as periodically or on demand (e.g., such as in glucose-on-demand (GoD) systems).

It should be appreciated that the initial reference time in the analyte point estimate and the analyte rate-of-change estimate described above (e.g., the glucose point and rate-of-change estimates described above) may correspond to the most recent data acquired in some instances; or alternatively, to some delayed time from the most recent data. Thus, for example, the glucose point estimate may be more generally represented by the following:

$$\hat{G}_b(k) = y(k - N_0) + \frac{a_1}{N_1 - N_0}[y(k - N_0) - y(k - N_1)] + \frac{a_2}{N_2 - N_0}[y(k - N_0) - y(k - N_2)]$$

wherein $N_0$ is an initial reference time, and the other parameter values similar to those previously described. Thus, after optimized parameter values have been selected and corresponding weighting coefficients calculated, lag-compensated point measurements may be calculated via the glucose point estimate, as shown below:

$$\hat{G}_1(k) = b_0 y(k-N_0) + b_1 y(k-N_1) + b_2 y(k-N_2)$$

The time delay to the first raw signal, $N_0$, may be chosen to be 0 in order to take advantage of the latest available measurement, for example. The other time delays, $N_1$ and $N_2$, may vary depending on application. $N_1$ and $N_2$ may be two different numbers in the order of 1 to 45 minutes, for example, but should not be interpreted as limited to such a time range.

Thus, the weighting coefficients $b_0$, $b_1$, and $b_2$ (derived based on the values selected for the parameters—$a_1$, $a_2$, $N_1$, $N_2$) may be applied to corresponding data at the initial reference time $N_0$, the first prior reference time $N_1$, and the second prior reference time $N_2$, respectively.

Similarly, the glucose rate-of-change estimate at any sample instance k may be more generally represented by the following, whose constants may have a different value:

$$\hat{G}_b(k) = \frac{c_1}{N_1 - N_0}[y(k - N_0) - y(k - N_1)] + \frac{c_2}{N_2 - N_0}[y(k - N_0) - y(k - N_2)]$$

After optimized parameter values have been selected and corresponding weighting coefficients calculated, lag-compensated rate-of-change measurements may be calculated via the glucose rate-of-change estimate, as shown below:

$$\hat{G}_1(k) = d_0 y(k-N_0) + d_1 y(k-N_1) + d_2 y(k-N_2)$$

Thus, for example, the weighting coefficients $d_0$, $d_1$, and $d_2$ (derived based on the values selected for the parameters—$c_1$, $c_2$, $N_1$, $N_2$) may be applied to corresponding data at the initial reference time $N_0$, the first prior reference time $N_1$, and the second prior reference time $N_2$, respectively.

In some aspects of the present disclosure, methods are provided that include both lag compensation of analyte point measurements and lag compensation of analyte rate-of-change measurements. For example, FIG. 5 illustrates a flowchart for a method of lag compensation of analyte point measurements and analyte rate-of-change measurements, according to one embodiment. The method includes common aspects to both methods above, and thus for the sake of clarity and brevity, common aspects will not be described in great detail again.

At block 505, reference analyte measurements are received. Again, the reference analyte measurements may be provided by a development set, for example. Parameter values may be selected to optimize the analyte point estimate and analyte rate-of-change estimate. For example, the parameter values for the analyte point estimate and analyte rate-of-change estimate may be determined by calculating error metrics.

Again, the analyte point estimate is based on a sum of an analyte point and a sum of a plurality of scaled rates-of-changes. The analyte point corresponds to measurements at an initial reference time. The rates-of-changes include a rate-of-change from the initial reference time to a first prior reference time, and another rate-of-change from the initial reference time to a second prior reference time that is different than the first prior reference time. Again, it should be appreciated that while two rates-of-changes are described, the analyte point estimate may include more than two rates-of-changes, such as three, four, five, or more rates of changes. The parameter values may include, for example, scalars for each of the rates-of-changes, as well as the prior reference times for each of the rate-of-changes.

Again, the analyte rate-of-change estimate is based on a sum of a plurality of scaled rates-of-changes. The rates-of-changes include a rate-of-change from the initial reference time to a first prior reference time, and another rate-of-change from the initial reference time to a second prior reference time that is different than the first prior reference time. Again, it should be appreciated that while two rates-of-changes are described, the analyte rate-of-change estimate may include more than two rates-of-changes, such as three, four, five, or more rates of changes, in other embodiments. The parameter values may include, for example, scalars for each of the rates-of-changes, as well as the prior reference times for each of the rate-of-changes. In one embodiment, the prior reference times in the analyte point estimate are the same as the prior reference times in the analyte rate-of-change estimate. In other embodiment, the prior reference times may differ.

Parameter values may be selected to optimize the analyte point estimate and analyte rate-of-change estimate. For example, the parameter values for the analyte point estimate and analyte rate-of-change estimate may be determined by calculating error metrics. At block 510, error metrics are calculated for a plurality of combinations of values as parameters in an analyte point estimate and analyte rate-of-change estimate. A set of parameter values for the analyte point estimate and a set of parameter values for the analyte rate-of-change estimate are then selected based on the calculated error metrics, as represented at block 520. Again, as previously described, the error metrics may be generated using various optimization routines (e.g., by calculating a sum-of-squared-errors, etc.). Furthermore, in one embodiment, the parameter values may be selected based on the smallest error metric.

After selecting the parameter values, a set of weighting coefficients for each estimate may be derived for the analyte point and rate-of-change estimates based on the selected sets of parameters, as represented by block 530. The sets of weighting coefficients are then implemented in a point filter and rate-of-change filter that may be used to calculate lag-compensated point and rate-of-change measurements by applying the corresponding sets of weighting coefficients to uncompensated analyte measurements (e.g., interstitial glucose measurements) received at the corresponding times of the filter (e.g., the most recent time and the selected time indices (prior reference times), as represented by block 535. Again, in one embodiment, the prior reference times in the analyte point estimate may be the same as the prior reference times in the analyte rate-of-change estimate. In other embodiments, the prior reference times may differ.

Multiple Filters

In some aspects of the present disclosure, multiple filters may be implemented. For example, multiple analyte point filters and/or multiple analyte rate-of-change filters may be implemented in parallel to enable different possible outputs.

While the optimized analyte estimates described above provide significant advantages, the method described above utilizes a specific number of sensor data points (e.g., in the example embodiment shown above, three data points are utilized—one at the initial reference time $N_0$, one at the first prior reference time $N_1$, and another at the second prior reference time $N_2$) to estimate the point and rate-of-change values of blood glucose at any given time. However, if any of the time indices (e.g., N0, N1, or N2) used contains invalid and/or unavailable data, then no output can be calculated, or may be difficult to determine accurately. As a result, data availability of a CGM device using this method may be low in some instances.

In one aspect of the present disclosure, parallel filters are provided to permit a robust estimation that is less susceptible to invalid and/or unavailable data. The parallel filters provide additional flexibility when invalid and/or unavailable data is present at a given time. For example, another parallel filter may be used for the lag-compensated output, or combinations of filters may be used to generate the lag-compensated output (e.g., by taking the average of any of the filters that generate an output at any given time). For example, the following may be implemented to represent 3 parallel glucose rate-of-change filters:

$$\hat{G}_1(k) = d_{0,1} y(k) + d_{1,1} y(k - N_{1,1}) + d_{2,1} y(k - N_{2,1})$$

$$\hat{G}_2(k) = d_{0,2} y(k) + d_{1,2} y(k - N_{1,2}) + d_{2,2} y(k - N_{2,2})$$

$$\hat{G}_3(k) = d_{0,3} y(k) + d_{1,3} y(k - N_{1,3}) + d_{2,3} y(k - N_{2,3})$$

where k is the sample time index of the sensor data; y is the calibrated sensor measurement; $N_{1,1}$ and $N_{2,1}$ are time delay indices for the first filter, and $d_{0,1}$, $d_{1,1}$, and $d_{2,1}$ are the weighting coefficients for the first filter (e.g. derived from values selected for corresponding parameter values—$c_{1,1}$, $c_{2,1}$, $N_{1,1}$, $N_{2,1}$—of the first analyte rate-of-change estimate); $N_{1,2}$ and $N_{2,2}$ are time delay indices for the second filter, and $d_{0,2}$, $d_{1,2}$, and $d_{2,2}$ are the weighting coefficients for the second filter (e.g. derived from values selected for corresponding parameters—$c_{1,2}$, $c_{2,2}$, $N_{1,2}$, $N_{2,2}$—of the second analyte rate-of-change estimate); and $N_{1,3}$ and $N_{2,3}$ are time delay indices for the third filter, and $d_{0,3}$, $d_{1,3}$, and $d_{2,3}$ are the weighting coefficients for the third filter (e.g. derived from values selected for corresponding parameters—$c_{1,3}$, $c_{2,3}$, $N_{1,3}$, $N_{2,3}$—of the third analyte rate-of-change estimate). It should be appreciated that while three filters are shown in the example embodiment, any other number of filters may be implemented in other embodiments e.g., 2 filters, 4 filters, 5 filters, etc.

The parameter values for the first, second, and third analyte rate-of-change estimates may be selected similarly as discussed above for the single filter. For example, error metrics may be similarly calculated for a plurality of combinations of values as parameters in the analyte rate-of-change estimates, and the parameter values selected based on the calculated error metrics. For example, in one embodiment, the first filter may be associated with a better error metric (e.g., smaller error metric) than the second filter, which is associated with a better error metric than the third filter.

By designing the parallel filter elements such that some of the time index triplets across the three elements—($N_{1,1}$, $N_{2,1}$, $N_{3,1}$), ($N_{1,2}$, $N_{2,2}$, $N_{3,2}$), ($N_{1,3}$, $N_{2,3}$, $N_{3,3}$) do not point to the same data, the filter can be made robust to intermittent missing data. Choosing staggered delays (e.g. ensuring that $N_1$, $N_2$, $N_3$ are unique for each filter) ensures that single invalid and/or unavailable data points will not cause all the filters to fail simultaneously. A missing data point may cause individual filters to fail, but the overall filter bank can still provide a final value. Note that the most recent data used in the parallel filter elements shown in the example above use a common point referring to the latest available value at any time, or put another way, the most recently received. In other embodiments, data robustness can be improved if the "latest point" (or most recently received) in the parallel filter elements is also staggered. However, depending on the application, it may be undesirable in some instances to compute any rate estimate in the absence of latest data. The exclusion of data staggering for the latest point is only one embodiment and is not to be implied to be a limitation of the present disclosure. For example, in some embodiments, some, but not all, of the time delay indices (prior reference times) of two filters may be the same. For example, in the embodiment above, the first and second filter may have the same first prior reference time ($N_1$ time index), but have a different second prior reference time ($N_2$ time index), or vice versa. Thus, the sets of parameter values for two filters may point to different sets of prior reference times for the outputs despite having a common prior reference time. This concept is also applicable when there are three or more filters present, and is also similarly applicable to analyte point estimates.

As uncompensated analyte measurements are received, which may include invalid and/or unavailable data intermittently, the blood glucose rate-of-change estimate may then be computed based on the output of one or more filters to generate lag-compensated rate-of-change measurements. For example, in one embodiment, lag-compensated rate-of-change measurements may be calculated, for example, as the average of any combination of the calculations of the filters that generates a result at any given time k. In another embodiment, lag compensated rate-of-change measurements may be chosen in an hierarchical order—e.g., from the first filter associated with the best error metric if valid data is available for the first filter; from the second filter associated with the second best error metric if valid data is not available for the first filter, but available for the second filter; and from the third filter with third best error metric if valid data is not available for the first and second filters, but available for the third filter. It should be appreciated that the preceding is exemplary, and that the lag-compensated rate-of-change measurements may be calculated from the three parallel filters in other various combinations, averages, weighted sums, etc.

In some embodiments, the time indices for the filters may be based on expected duration of data unavailability. For example, in one embodiment, the first filter is picked following the method outlined above for the single filter. The time index set for the second filter is picked such that at least one of the time indices (prior reference times) is different from that of the first set, in a manner which allows for that time index to be far enough from the perspective of expected data unavailability duration, and such that there exist an optimal parameter set that allows the glucose rate-of-change estimates to be viable from the perspective of metrics outlined in the single filter example.

For example, in one embodiment, two samples may be a likely duration of missing data that needs to be mitigated for. Then, at least one time delay index (prior reference time) in the second filter is set to be two samples away from that of the first filter. In addition, the resulting optimal parameter combination results in a glucose rate-of-change estimate that generate a similar performance as determined by the optimization procedure outlined in the single filter embodiment.

A similar analysis can be made for the analyte point estimate (e.g., glucose point estimate), where an array of parallel filter elements is used, and then one or more available outputs may be used. For example, the following may be implemented to represent 3 parallel glucose point filters:

$$\hat{G}_1(k) = b_{0,1} y(k) + b_{1,1} y(k - N_{1,1}) + b_{2,1} y(k - N_{2,1})$$

$$\hat{G}_2(k) = b_{0,2} y(k) + b_{1,2} y(k - N_{1,2}) + b_{2,2} y(k - N_{2,2})$$

$$\hat{G}_3(k) = b_{0,3} y(k) + b_{1,3} y(k - N_{1,3}) + b_{2,3} y(k - N_{2,3})$$

where k is the sample time index of the sensor data; y is the calibrated sensor measurement; $N_{1,1}$ and $N_{2,1}$ are time delay indices for the first filter, and $b_{0,1}$, $b_{1,1}$, and $b_{2,1}$ are the weighting coefficients for the first filter (e.g., derived from values selected for corresponding parameter values—$a_{1,1}$, $a_{2,1}$, $N_{1,1}$, $N_{2,1}$—of the first analyte rate-of-change estimate); $N_{1,2}$ and $N_{2,2}$ are time delay indices for the second filter, and $b_{0,2}$, $b_{1,2}$, and $b_{2,2}$ are the weighting coefficients for the second filter (e.g., derived from values selected for corresponding parameters—$a_{1,2}$, $a_{2,2}$, $N_{1,2}$, $N_{2,2}$—of the second analyte rate-of-change estimate); and $N_{1,3}$ and $N_{2,3}$ are time delay indices for the third filter, and $b_{0,3}$, $b_{1,3}$, and $b_{2,3}$ are the weighting coefficients for the third filter (e.g., derived from values selected for corresponding parameters—$a_{1,3}$, $a_{2,3}$, $N_{1,3}$, $N_{2,3}$—of the third analyte rate-of-change estimate). Again, it should be appreciated that while three filters are shown in the example embodiment, any other number of filters may be implemented in other embodiments—e.g., 2 filters, 4 filters, 5 filters, etc.

The parameter values for the first, second, and third analyte point estimates may be selected, as similarly discussed above. Again, common aspects are not described again in detail. Furthermore, as uncompensated analyte measurements are received, which may include invalid and/or unavailable data intermittently, the blood glucose point estimate may then be computed based on the output of one or more filters to generate lag-compensated point measurements, as similarly discussed above.

It should be appreciated that for embodiments where both the analyte point estimate and the analyte rate-of-change estimate are implemented, parallel filters may be implemented for the analyte point estimate and/or the analyte rate-of-change estimate. It should be appreciated that in some instances, the time delay indices as well as the coefficients of the analyte point estimate may be very different from that of the analyte rate-of-change estimate.

Figure 6:
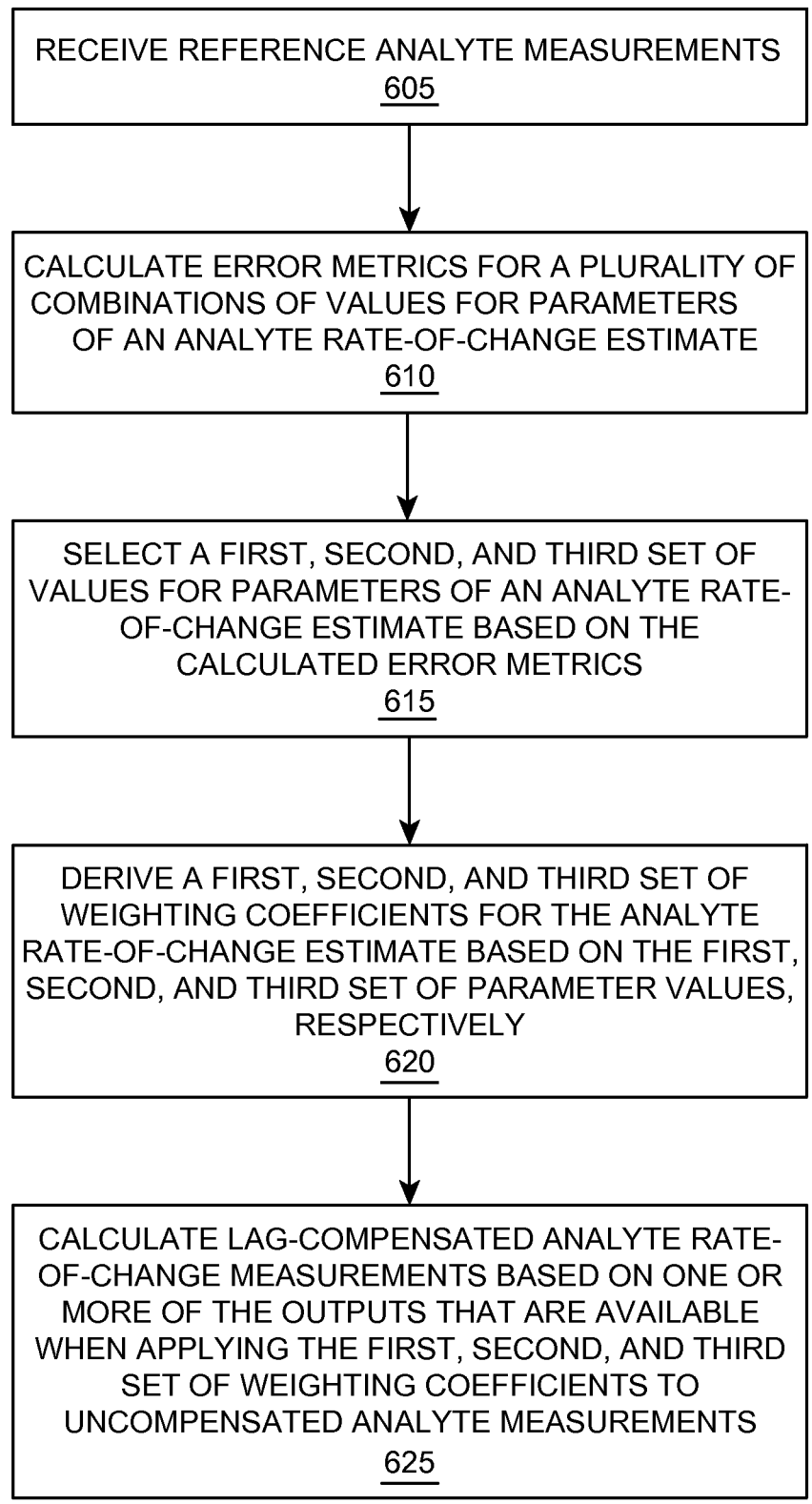
FIG. 6 illustrates a flowchart for a method of lag-compensation of analyte rate of change measurements with multiple analyte rate-of-change filters, according to one embodiment.

FIG. 6 illustrates a flowchart for a method of lag-compensation of analyte rate of change measurements with three analyte rate-of-change filters, according to one embodiment. It should be appreciated that similar methods for other number of filters (e.g., two, four, five, etc.) may be similarly implemented in other embodiments. Again, for the sake of clarity and brevity, common aspects will not be described in great detail again.

At blocks 605, reference analyte measurements are received. At block 610, error metrics are calculated for a plurality of combinations of values as parameters in an analyte rate-of-change estimate. Three sets of parameter values are then selected based on the calculated error metrics, as represented at block 615. After selecting the sets of parameter values, a first, second, and third set of weighting coefficients are derived using the first, second, and third set of parameter values, respectively, as represented by block 620. The weighting coefficients are then implemented in three rate-of-change filters that may be used to calculate lag-compensated rate-of-change measurements using the uncompensated analyte measurements (e.g., interstitial glucose measurements), as represented by block 625. For example, as described earlier, the available lag-compensated measurements may be averaged, may be hierarchically selected, etc.

Figure 7:
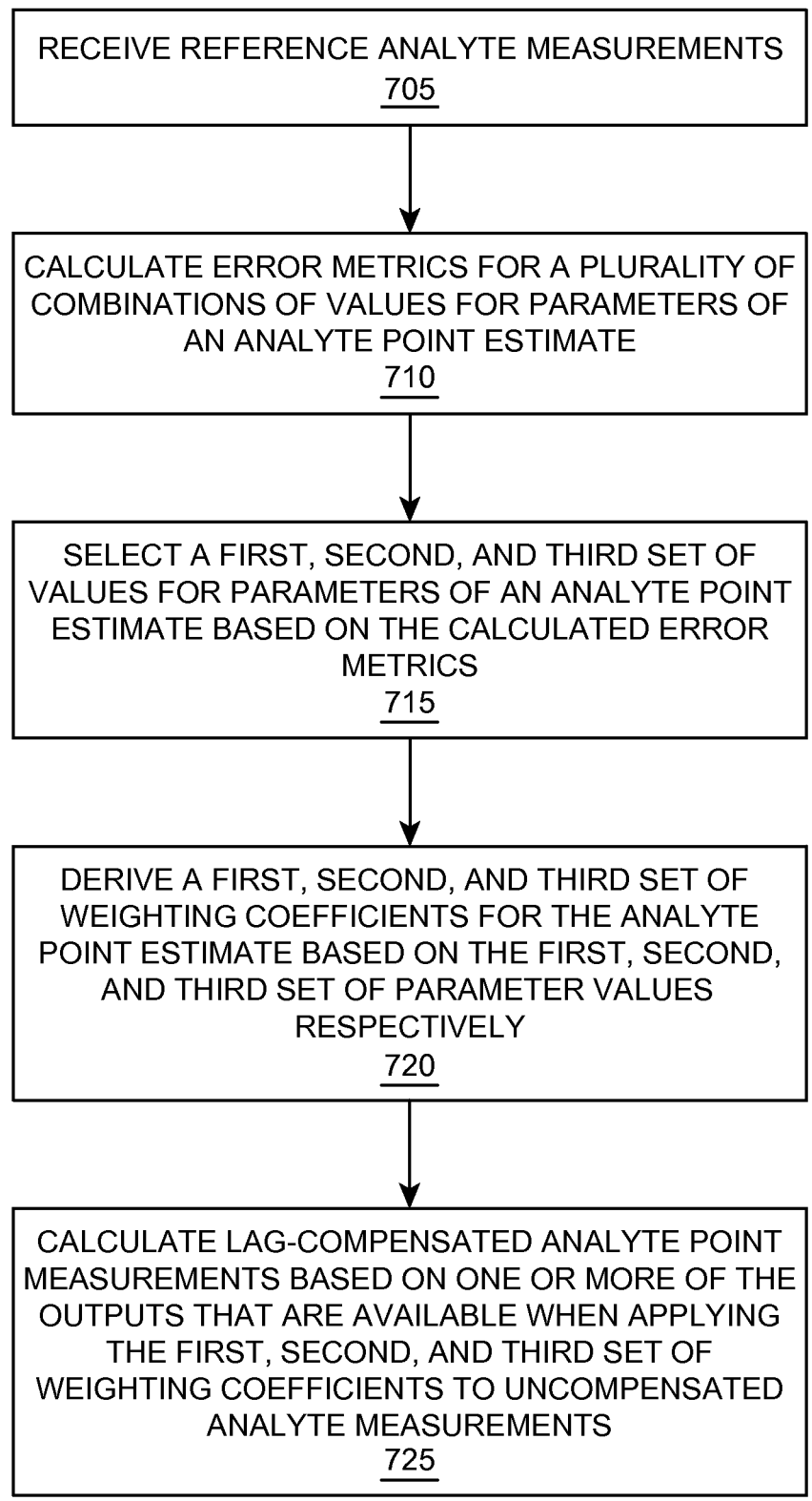
FIG. 7 illustrates a flowchart for a method of lag-compensation of analyte point measurements with multiple analyte point filters, according to one embodiment.

FIG. 7 illustrates a flowchart for a method of lag-compensation of analyte point measurements with three analyte point filters, according to one embodiment. It should be appreciated that similar methods for other number of filters (e.g., two, four, five, etc.) may be similarly implemented in other embodiments. For the sake of clarity and brevity, common aspects will not be described in great detail again.

At blocks 705, reference analyte measurements are received. At block 710, error metrics are calculated for a plurality of combinations of values as parameters in an analyte point estimate. Three sets of parameter values are then selected based on the calculated error metrics, as represented at block 715. After selecting the sets of parameter values, a first, second, and third set of weighting coefficients are derived using the first, second, and third set of parameter values, respectively, as represented by block 720. The weighting coefficients are then implemented in three point filters that may be used to calculate lag-compensated point measurements using the uncompensated analyte measurements (e.g., interstitial glucose measurements), as represented by block 725. For example, as described earlier, the available lag-compensated measurements may be averaged, may be hierarchically selected, etc.

Figure 8:
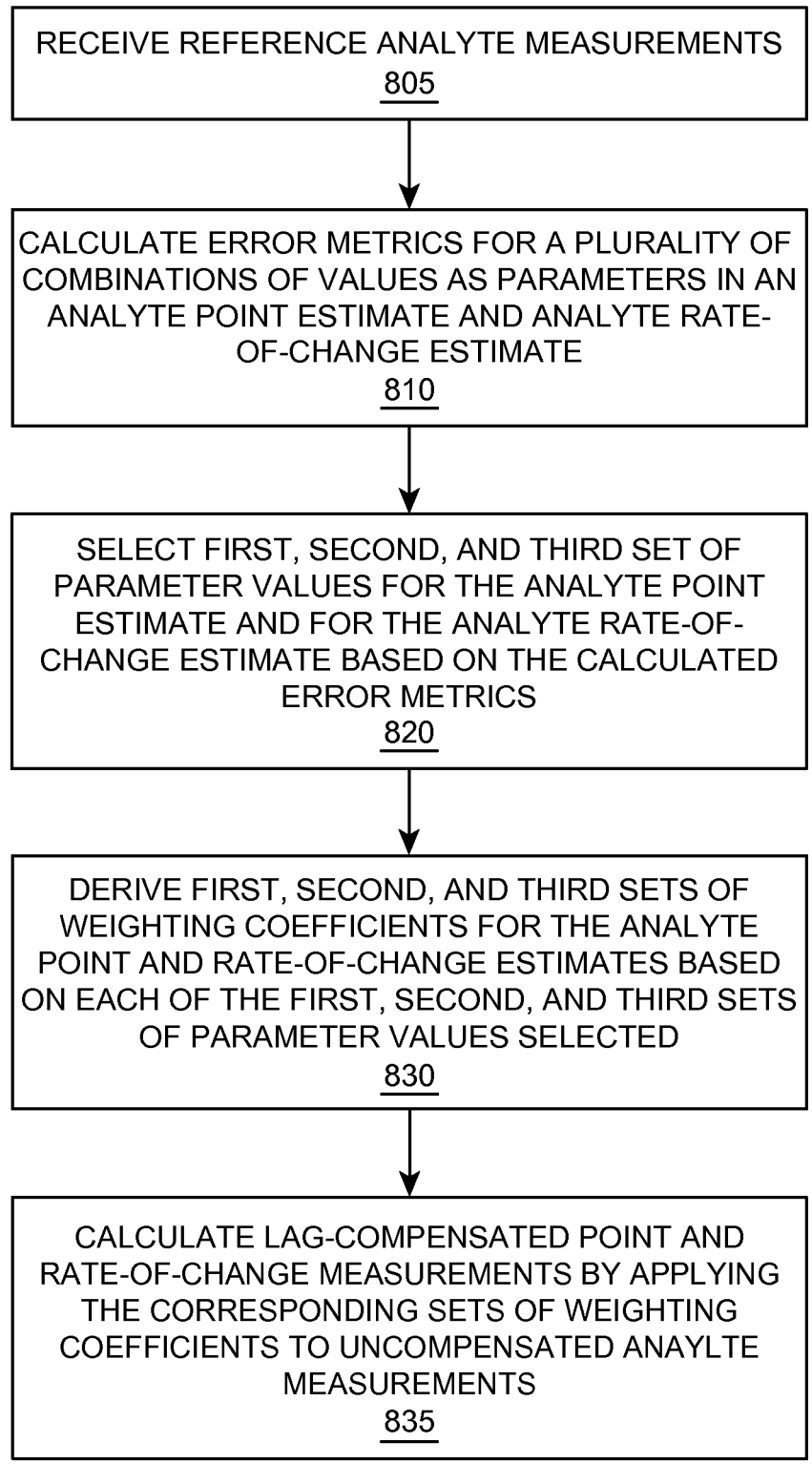
FIG. 8 illustrates a flowchart for a method of lag-compensation of analyte point and rate-of-change measurements with multiple analyte point filters and multiple analyte rate-of-change filters, according to one embodiment.

FIG. 8 illustrates a flowchart for a method of lag-compensation of analyte point and rate-of-change measurements with three analyte point filters and three analyte rate-of-change filters, according to one embodiment. It should be appreciated that similar methods for other number of filters (e.g., two, four, five, etc.) may be similarly implemented in other embodiments. For the sake of clarity and brevity, common aspects will not be described in great detail again.

At block 805 reference analyte measurements are received. The parameter values are selected to optimize the analyte point estimate and analyte rate-of-change estimate. For example, parameter values for the analyte point estimate and analyte rate-of-change estimate may be determined by calculating error metrics. At block 810, error metrics are calculated for a plurality of combinations of values as parameters in an analyte point estimate and analyte rate-of-change estimate. A first, second, and third set of parameter values for the analyte point estimate and a first, second, and third set of parameter values for the analyte rate-of-change estimate are then selected based on the calculated error metrics, as represented at block 820. Again, as previously described, the error metrics may be generated using various optimization routines (e.g., by calculating a sum-of-squared-errors, etc.). Furthermore, in some embodiments, the parameter values may be selected based on the smallest error metric.

First, second, and third sets of weighting coefficients are then derived based on corresponding first, second, and third sets of parameter values selected for the analyte point and rate-of-change estimates, as represented by block 830. The sets of weighting coefficients are then implemented in analyte point filters and analyte rate-of-change filters that may each be used to calculate lag-compensated point measurements and lag-compensated rate-of-change measurements by applying the corresponding sets of weighting coefficients to uncompensated analyte measurements (e.g., interstitial glucose measurements) received at the corresponding times of each filter (e.g., the most recent time and the selected time indices (prior reference times), as represented by block 835.

As uncompensated analyte measurements are received, which may include invalid and/or unavailable data intermittently, the lag-compensated point and rate-of-change measurements may be calculated based on the output of one or more point and rate-of-change filters with valid data present, respectively. For example, in one embodiment, lag-compensated rate-of-change measurements and lag-compensated point measurements may be calculated, as the average of any combination of the calculations of the respective rate-of-change and point filters that generate a result at any given time k. In another embodiment, lag-compensated rate-of-change measurements and lag-compensated point measurements may be chosen in an hierarchical order—e.g., from the respective first rate-of-change and point filter associated with the best error metric if valid data is available for the first filter; from the respective second rate-of-change and point filter associated with the second best error metric if valid data is not available for the first filter, but available for the second filter; and from the respective third rate-of-change and point filter with third best error metric if valid data is not available for the first and second filters, but available for the third filter.

It should be appreciated that the preceding is exemplary, and that the lag-compensated rate-of-change measurements may be calculated from the three parallel filters in other various combinations, averages, weighted sums, etc. Furthermore, in one embodiment, the prior reference times in the analyte point estimate may be the same as the prior reference times in the analyte rate-of-change estimate. In other embodiments, the prior reference times may differ. It should also be appreciated that the analyte point filters are independent of the analyte rate-of-change filters and may be configured differently from one another.

EXAMPLE

The following is provided as an exemplary illustration, and should not be interpreted as limiting. The glucose point estimate at any sample instance k is estimated by the average of any of the available filter outputs:

$\hat{G}_1(k)=1.73y(k)-0.30y(k-7)-0.46y(k-14)$ $\hat{G}_2(k)=1.77y(k)-0.28y(k-6)-0.53y(k-13)$ $\hat{G}_3(k)=1.85y(k)-0.31y(k-5)-0.57y(k-12)$ Similarly, the glucose rate estimate at any sample instance k is estimated by the average of any of the available filter outputs:

$\hat{G}_1(k)=0.074y(k)-0.051y(k-7)-0.023y(k-14)$ $\hat{G}_2(k)=0.085y(k)-0.056y(k-5)-0.029y(k-14)$ $\hat{G}_3(k)=0.086y(k)-0.051y(k-5)-0.035y(k-12)$ Multiple Banks Temporal sensor artifacts known as dropouts may cause the raw sensor reading to read abnormally low for a period of time, but may remain in a physiologically valid range of glucose concentration values. In some instances, algorithms that mitigate lag may further exacerbate this problem by being more sensitive to the rapid changes in blood glucose caused by these dropouts compared to an algorithm that does not attempt to mitigate lag. In such case, the system may predict a significantly lower value during the initial phase of the dropout (negative overshoot) and a significantly higher value during the recovery phase of the dropout (positive overshoot).

Figure 9:
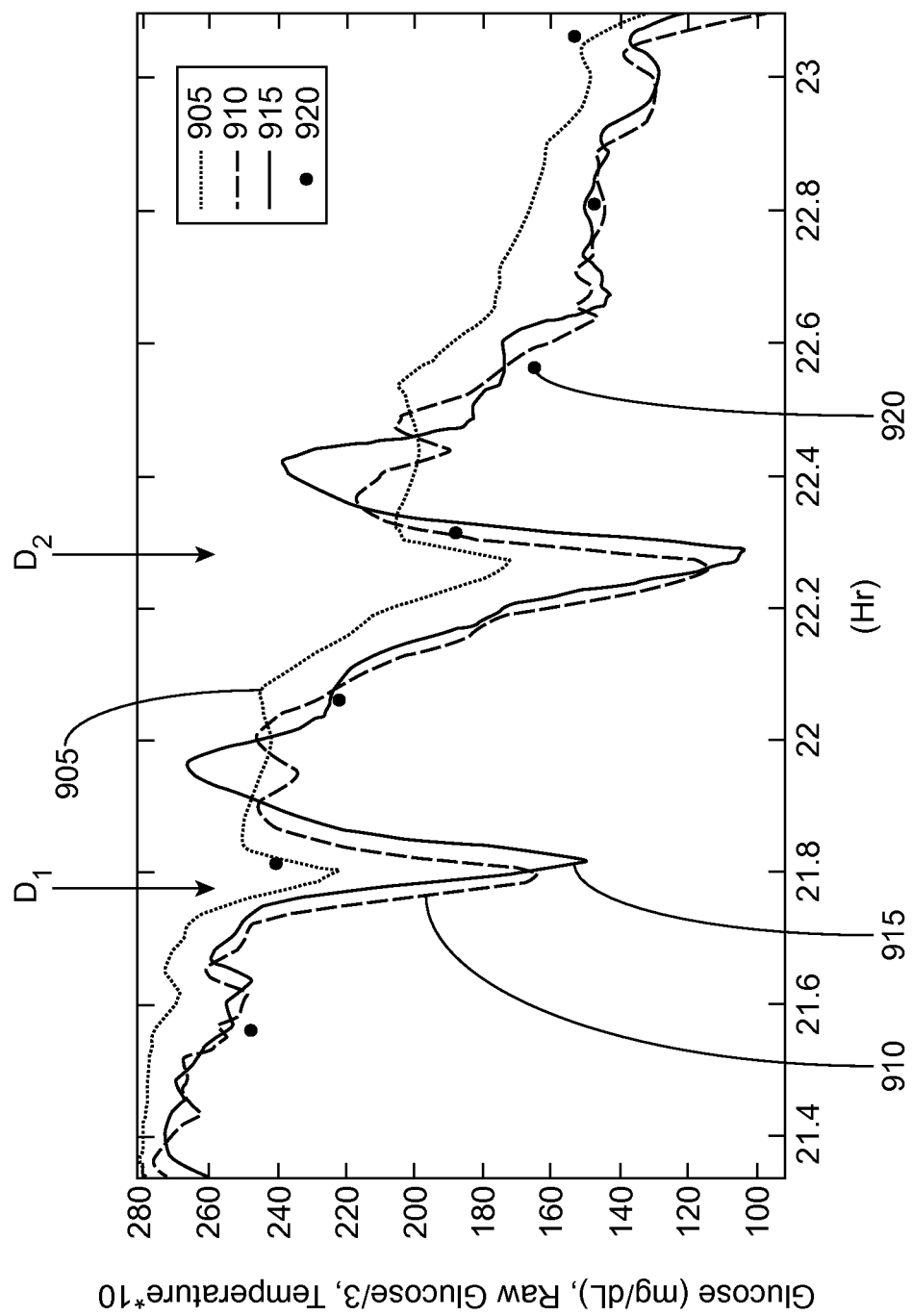
FIG. 9 illustrates a graph of an example analyte measurement plot having dropouts.

FIG. 9 illustrates a graph of an example analyte measurement plot having dropouts. Line 905 shows uncompensated glucose measurements (e.g., received from an implanted glucose sensor) having dropouts, as indicated at the two dips D1 and D2. The time scale is shown in hours.

Lines 910 and 915 illustrate example lag-compensated measurements and their corresponding dropouts at D1 and D2. As shown, the lag-corrected signal includes negative and positive overshoot observed around the onset and recovery of the dropouts at D1 and D2. Points 920 illustrate the YSI reference glucose measurements (e.g., standard reference measurements from blood samples) measured approximately every 15 minutes. In the graph shown, the lag correction improves sensor accuracy in general, but may degrade accuracy around dropouts. This is especially crucial in the hypoglycemic range.

In some aspects of the present disclosure, multiple banks are implemented to mitigate temporal sensor artifacts, such as dropouts, invalid, physiologically infeasible, or missing data. As will be demonstrated below, the aggressiveness of lag correction is dynamically adjusted based on a temporal noise metric that detects the presence of transient glucose rates of change that is physiologically infeasible.

In some aspects of the present disclosure, a second analyte rate-of-change estimate (and/or a second analyte point estimate) is provided. The second estimate includes a time delay from the first estimate such that the most recent sensor data for the second estimate will be delayed from the most recent sensor data for the first estimate.

For example, as described earlier, the glucose rate-of-change estimate may be represented as follows:

$\hat{G}_1(k)=d_0y(k-N_0)+d_1y(k-N_1)+d_2y(k-N_2)$

And, the glucose point estimate may be represented as follows:

$\hat{G}_1(k)=b_0y(k-N_0)+b_1y(k-N_1)+b_2y(k-N_2)$

While only a single filter for each is shown for the sake of clarity and brevity, it should be appreciated that multiple banks may also be implemented with multiple filters. Further, it should be appreciated that while the following is described in the context of an additional bank, any number of additional banks may be implemented in various embodiments.

In one embodiment, the second analyte rate-of-change estimate is generated with the latest sensor value used being a value that is delayed $M_0$ steps behind (at any given time k). The following represents an example second analyte rate-of-change estimate delayed by $M_0$:

$$\hat{G}_{2T}(k) = e_0 y(k-M_0) + e_1 y(k-M_1) + e_2 y(k-M_2)$$

$$M_2 > M_1 > M_0$$

wherein k is the sample time index of the sensor data; y is the calibrated sensor measurement; $e_0$, $e_1$, and $e_2$ are scalars, and $M_0$, $M_1$, and $M_2$ are time delay indices. While $N_0$ in the first estimate refers to an initial reference time (e.g., as shown equal to 0 for the most recent data), $M_0$ in the second estimate refers to an alternate initial reference time that is delayed by $M_0$ from the initial reference time. $M_1$ is a prior reference time that is delayed from $M_0$, and $M_2$ is a prior reference time that is delayed form $M_1$.

Similarly, the second analyte point estimate may be represented as follows:

$$\hat{G}_{2T}(k) = f_0 y(k-M_0) + f_1 y(k-M_1) + f_2 y(k-M_2)$$

$$M_2 > M_1 > M_0$$

wherein k is the sample time index of the sensor data; y is the calibrated sensor measurement; $f_0$, $f_1$, and $f_2$ are scalars, and $M_0$, $M_1$, and $M_2$ are time delay indices. Again, while $N_0$ in the first estimate refers to an initial reference time (e.g., as shown equal to 0 for the most recent data), $M_0$ in the second estimate refers to an alternate initial reference time that is delayed by $M_0$ from the initial reference time. $M_1$ is a prior reference time that is delayed from $M_0$, and $M_2$ is a prior reference time that is delayed form $M_1$.

It should be appreciated that in other embodiments, the initial reference time of the first estimate may be a non-zero value (i.e., includes an $N_0$ initial time delay), in which case the alternate initial time delay of the second estimate ($M_0$) would be greater than the non-zero value of the first estimate.

It should be appreciated that in some instances, each set of the reference times for the analyte point estimates (and/or analyte rate-of-change estimates) is unique as a whole. In other words, two (or more) banks may include one or more reference times in common, but the set of reference times as a whole should be as unique in that not all in one set are identical to all in another set.

Intuitively, the second estimate may not perform as well as the first estimate on aggregate because in the majority of time, where dropouts are nonexistent, estimating blood glucose using more recent measurements typically yield more accurate results than using less recent measurements. However, provided that the delay $M_0$ is not extremely large, both the first estimate and the second estimate may produce similar results.

When $M_0$ is small enough so that both the first estimate and the second estimate generally produce similar results, but $M_0$ is large enough to be relatively larger than the duration of the onset and/or recovery of dropouts, a large deviation between the first estimate and the second estimate can be used to infer the presence of a dropout. Example durations of dropouts may range from 1 to 50 minutes, such as including 1 to 15 minutes. Example durations of time delay (M0) may range from 1 to 45 minutes, such as including 1 to 10 minutes.

The following is a description of an example embodiment that employs this principle of transient parity between instantaneous-information and delayed-information based estimates. While the following is illustrated for glucose point estimates, it should be appreciated that it may be similarly applicable to glucose rate-of-change estimates.

In one embodiment, the first glucose point estimate (e.g., the first bank, designated as primary bank) has each of its component filters contain an initial reference time corresponding to a short delay (e.g. 0 minutes, the most recent point). This will allow the primary bank to quickly react to transient artifacts. The primary bank generates $G_1$, an estimate at any sample time k.

The second glucose point estimate (e.g., a second bank, designated as secondary bank) has the shortest delay in its component filters to be some period of time based on the projected size of the artifacts onset and/or recovery (e.g. represented as $N_{VART}$ below). The secondary bank generates a second estimate $G_{2T}$, at any sample time k. At each time step, a moving average of the difference between the outputs of these banks (i.e. $G_1-G_{2T}$) from the most recent $N_{VART}$ minutes is computed. The primary bank will follow the transient artifacts in the raw glucose data, while the secondary bank will not be affected based on its delayed reaction time. This moving average difference may then be scaled by a capped average of CGM points in the recent past (i.e. present to $N_{VART}-1$ minutes in the past). In other words, the moving average difference is divided by the smaller of either a predetermined cap, $G_{ST}$, or the average of CGM points in the past $N_{VART}$ minutes. Finally, a scaling factor $K_{VART}$ may be applied when necessary to be combined with other metrics. The described variance may be represented by the following:

$$\sigma_T^2(k) = K_{VART} \frac{\frac{1}{N_{VART(VALID)}} \sum_{j=0}^{N_{VART}-1} [G_1(k-j) - G_{2T}(k-j)]^2}{\min\left(G_{ST}, \frac{1}{N_{VART(VALID)}} \sum_{j=0}^{N_{VART}-1} y(k-j)\right)}$$

Thus, the three parameters primarily determine the response to transient artifacts. The difference between $G_1$ and $G_{2T}$ largely establishes the magnitude of the noise metric. A larger window would lead to a larger metric, as the secondary bank would remain relatively unchanged while the primary bank reacted to the transient. A larger averaging window $N_{VART}$ causes these changes to persist, leading to a noise metric that tends to remain high for a longer period of time. Finally, a scaling factor $K_{VART}$ determines the magnitude of the final response. These parameters are selected, for example, based on the magnitude and duration of the transient artifacts that are to be identified The result is a metric $\sigma_T^2$ that reacts quickly to fast transient artifacts and remains high for some time, based on the differences in the minimum delays of the two banks. The metric can then be used to weight the extent of lag correction based on the presence of transient artifacts.

The following illustrates one example method of weighting the outputs. It should be appreciated that other methods may be implemented between banks in other embodiments. A third bank $G_{2S}$ is defined, in which the calculation is made to be less sensitive to the negative effects of transient artifacts at the expense of reduced nominal accuracy relative to the first (and preferred) bank $G_1$. For example, $G_{2S}$ can be a weighted average of the most recent $N_{SLOW}$ sensor values, where the weights are derived from the auto-correlation function of reference glucose data or synthesized using other methods. This does not preclude setting $G_{2S}$ equal to $G_{2T}$ in one embodiment.

Given the first bank, $G_1$, and a third bank, $G_{2S}$, and the metric $\sigma_T^2$ to estimate the severity of a transient artifact, the blood glucose estimate at any time k can be written as a weighted sum between the two banks.

$$\hat{G}_b(k) = \begin{cases} [w_1(k)G_1(k)] + [w_2(k)G_{2S}(k)] & \text{if } G_1(k) \text{ and } G_{2S}(k) \text{ are available} \\ G_1(k) & \text{if } G_{2S}(k) \text{ is unavailable} \\ G_{2S}(k) & \text{if } G_1(k) \text{ is unavailable} \end{cases}$$

wherein the weight for the first term is made to approach 0 when $\sigma_T^2$ is large, and made to approach 1 when $\sigma_T^2$ is small. One example is to use a baseline value $\sigma_{T_o}^2$ computed a priori, whose value is typically in the same order as $\sigma_T^2$ when no transient artifact occurs. The normalization can then be scaled by a power P, which can be used to adjust the sensitivity of the weight $w_1$. For example, setting P at a higher value (e.g. 4 instead of 1) makes the weight $w_1$ drop faster to 0 when transients occur.

$$w_1(k) = \frac{1}{1 + \left[\frac{\sigma_T^2(k)}{\sigma_{T_o}^2}\right]^P}$$

wherein the weight for the second term is such that the sum of the weights equal to 1: $w_1 + w_2 = 1$. It should be understood that variations can be made to consider recent past availability of $G_1$ and $G_{2S}$ in addition to their latest availability.

Figure 10:
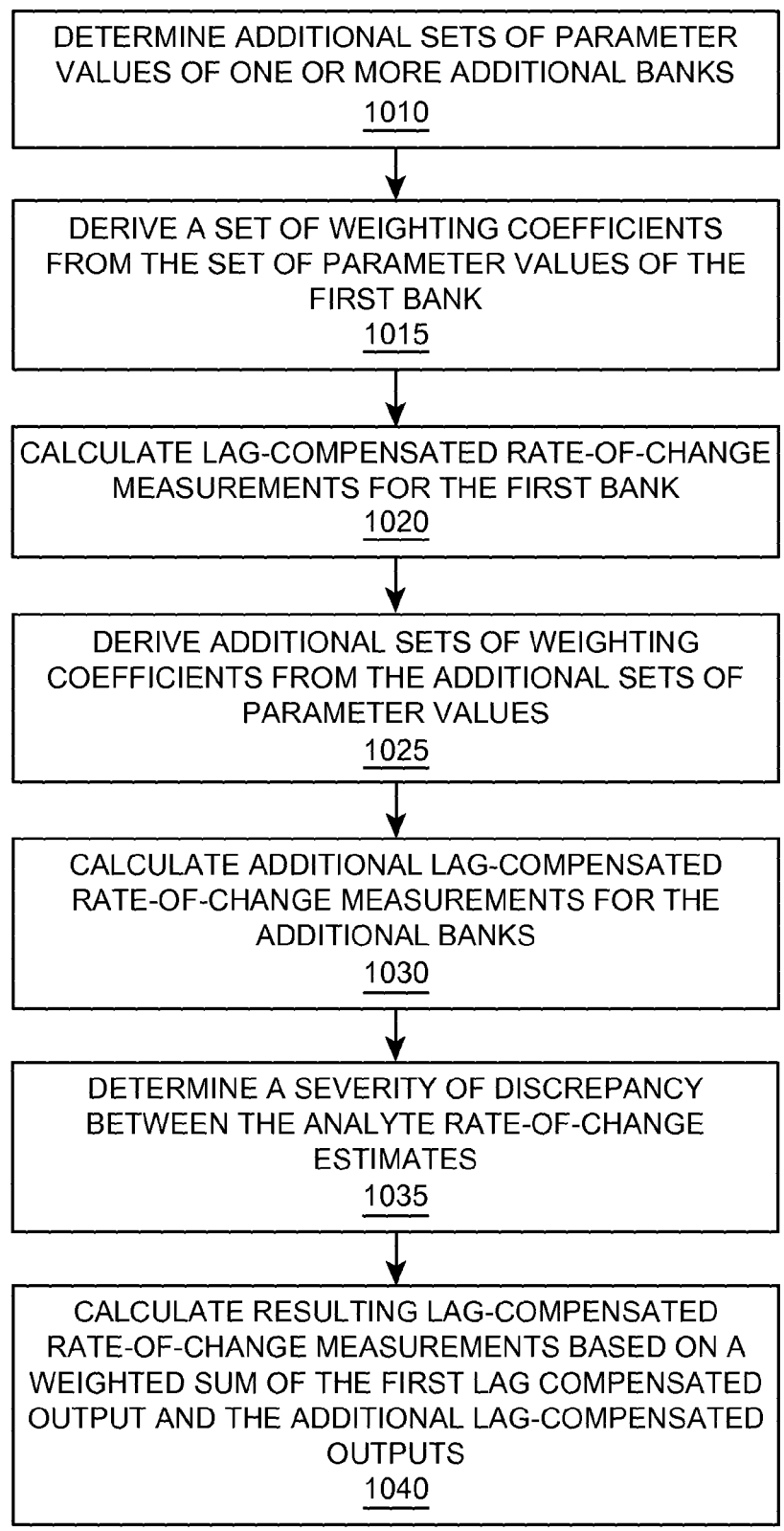
FIG. 10 illustrates a flowchart for a method of lag compensation of analyte rate-of-change measurements with multiple banks, according to one embodiment.

FIG. 10 illustrates a flowchart for a method of lag compensation of analyte rate-of-change measurements with multiple banks, according to one embodiment. The method in FIG. 10 may be implemented, for example, with respect to the method shown in FIG. 3, and reference to the method in FIG. 3 is made. It should be appreciated, that the principles may be similarly and equally applicable to FIG. 6.

At block 1010, additional sets of parameter values are determined for additional analyte rate-of-change estimates. The additional analyte rate-of-change estimates are based on sums of a plurality of scaled rates-of-changes. The plurality of scaled rates-of-changes for each of the additional analyte rate-of-change estimates are from an alternate initial reference time to prior reference times with respect to the alternate initial reference time. The alternate initial reference time is prior to the initial reference time by a time delay. For instance, the time delay may be predetermined based on a projected size of artifacts.

For example, referring back to FIG. 3, if a second bank was implemented, another set of parameter values for a second analyte rate-of-change estimate is determined. In the second estimate, however, the rates-of-changes are from an alternate initial reference time to two different prior reference times respectively. The alternate initial reference time is selected such that it is prior to the initial reference time in the first bank, and thus is delayed from the first bank.

At block 1015, a set of weighting coefficients is derived from the set of parameter values of the first bank (e.g., from FIG. 3). At block 1020, lag-compensated rate-of-change measurements are calculated for the first bank. For example, first lag-compensated rate-of-change measurements are calculated from the uncompensated analyte measurements by applying the set of weighting coefficients of the first bank to corresponding uncompensated analyte measurements received at the initial reference time and prior reference times of the set of parameter values of the first bank (e.g., from FIG. 3).

At block 1025, additional sets of weighting coefficients are derived from the additional sets of parameter values. At block 1030, lag-compensated rate-of-change measurements are calculated for the additional banks. For example, additional lag-compensated rate-of-change measurements are calculated from the uncompensated analyte measurements by applying the additional sets of weighting coefficients to corresponding uncompensated analyte measurements received at the alternate initial reference time and at the prior reference times of each of the additional sets of parameter values.

For example, referring back to the example of FIG. 3 and the second bank, a second set of weighting coefficients are derived from the parameter values selected for the second analyte rate-of-change estimate. These weighting coefficients are accordingly applied to the uncompensated analyte measurements that are received at the alternate initial reference time and at the prior reference times of the second bank, in order to calculate lag-compensated rate-of-change measurements associated with the second bank.

At block 1035, a severity of discrepancy is determined between the analyte rate-of-change estimates. At block 1040, resulting lag-compensated rate-of-change measurements are calculated based on a weighted sum of the lag compensated output of the first bank and the additional lag-compensated outputs of the additional banks. The weighted sum is based on the severity of discrepancy.

For example, in the example of FIG. 3 and the second bank, a severity of discrepancy between the two lag-compensated rate-of-change measurements for the first and second bank is determined and used to calculate resulting lag-compensated rate-of-change measurements. For example, as described above, a weighted sum of the two outputs may be based on the severity of discrepancy.

Figure 11:
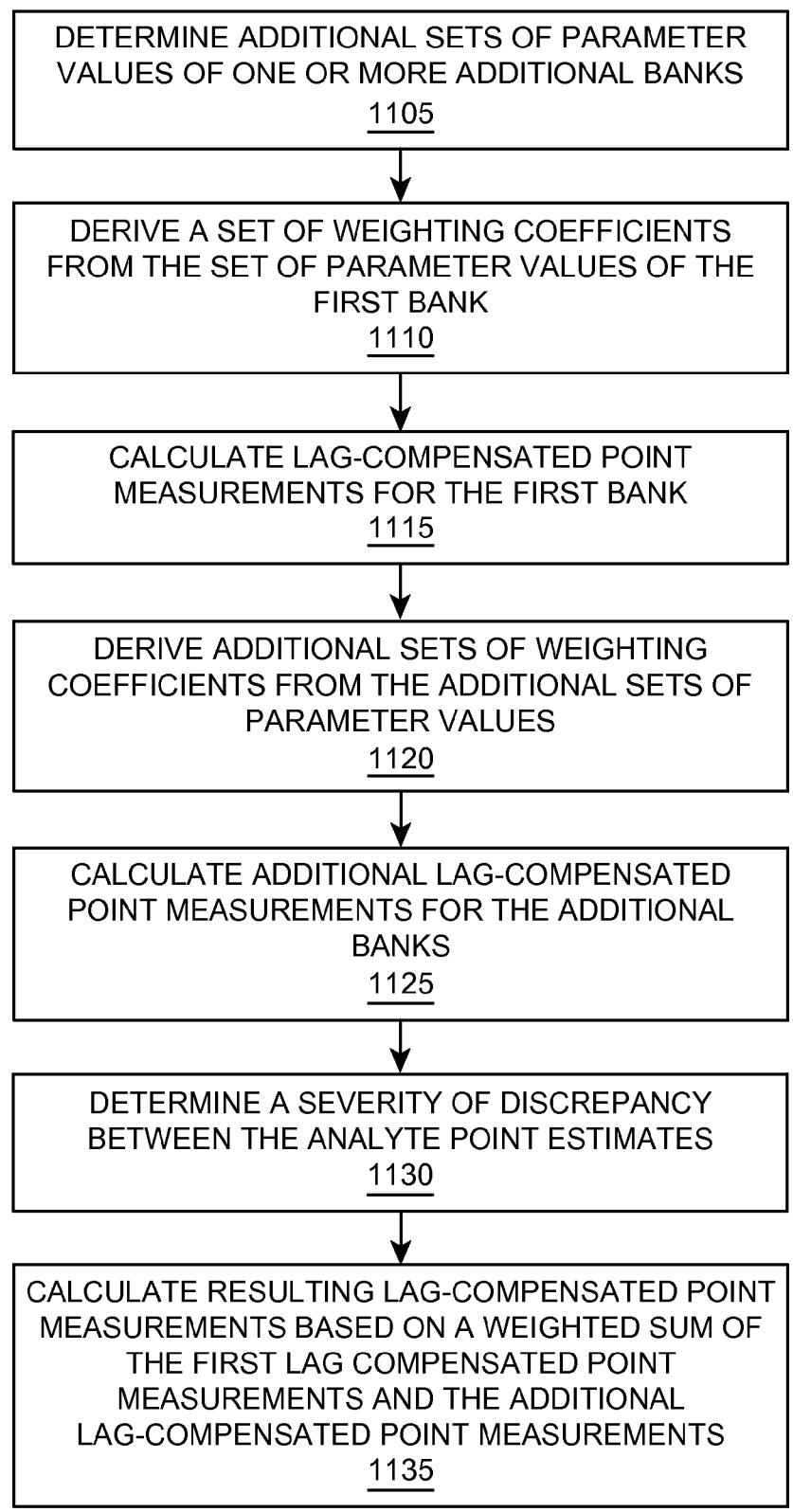
FIG. 11 illustrates a flowchart for a method of lag compensation of analyte point measurements with multiple banks, according to one embodiment.

FIG. 11 illustrates a flowchart for a method of lag compensation of analyte point measurements with multiple banks, according to one embodiment. The method in FIG. 11 may be implemented, for example, with respect to the method shown in FIG. 4, and reference is made to FIG. 4. It should be appreciated, that the principles may be similarly and equally applicable to FIG. 7.

At block 1105, additional sets of parameter values for one or more additional analyte point estimates are determined. The additional analyte point estimates are based on sums of an analyte point and sums of a plurality of scaled rates-of-changes. The analyte point corresponds to measurements at an alternate initial reference time that is prior to the initial reference time of the first analyte point estimate for the first bank by a time delay. For example, the time delay may be predetermined based on an assumed distribution of duration and size of artifacts. The plurality of scaled rates-of-changes for each of the additional analyte point estimates are from the alternate initial reference time to various prior reference times with respect to the alternate initial reference time.

For example, referring back to FIG. 4 and the second bank, another set of parameter values for a second analyte point estimate is determined. The second estimate, however, includes an analyte point corresponding to an alternate initial reference time that is prior the initial reference time by a time delay. In this way, the second bank is delayed from the first bank. Furthermore, the rates-of-changes for the second estimate are from an alternate initial reference time to two different prior reference times respectively. The alternate initial reference time is selected such that it is prior to the initial reference time in the first bank, and thus is delayed from the first bank.

At block 1110, a set of weighting coefficients is derived from the set of parameter values of the first bank (e.g., from FIG. 4). At block 1115, lag-compensated point measurements for the first bank are calculated. For example, lag-compensated point measurements are calculated from the uncompensated analyte measurements by applying the set of weighting coefficients of the first bank to corresponding uncompensated analyte measurements received at the initial reference time and the prior reference times of the set of parameter values of the first bank (e.g., from FIG. 4).

At block 1120, additional sets of weighting coefficients are derived from the additional sets of parameter values. At block 1125, additional lag-compensated point measurements for the additional banks are calculated. For example, additional lag-compensated point measurements are calculated from the uncompensated analyte measurements by applying the additional sets of weighting coefficients of the additional banks to corresponding uncompensated analyte measurements received at the alternate initial reference time and at the prior reference times of each of the additional sets of parameter values.

For example, referring back to the example of FIG. 4 and the second bank, a set of weighting coefficients for the second bank are derived from the parameter values selected for the second analyte point estimate. These weighting coefficients are accordingly applied to the uncompensated analyte measurements that are received at the alternate initial reference time and at the prior reference times of the second bank, in order to calculate lag-compensated point measurements associated with the second bank.

At block 1130, a severity of discrepancy is determined between the analyte point estimates. At block 1135, resulting lag-compensated point measurements are calculated based on a weighted sum of the lag compensated point measurements of the first bank and the additional lag-compensated point measurements of the additional banks. The weighted sum is based on the severity of discrepancy.

For example, in the example of FIG. 4 and the second bank, a severity of discrepancy between the two lag-compensated point measurements for the first and second bank is determined and used to calculate resulting lag-compensated point measurements. For example, as described above, a weighted sum of the two outputs may be based on the severity of discrepancy.

Figure 12:
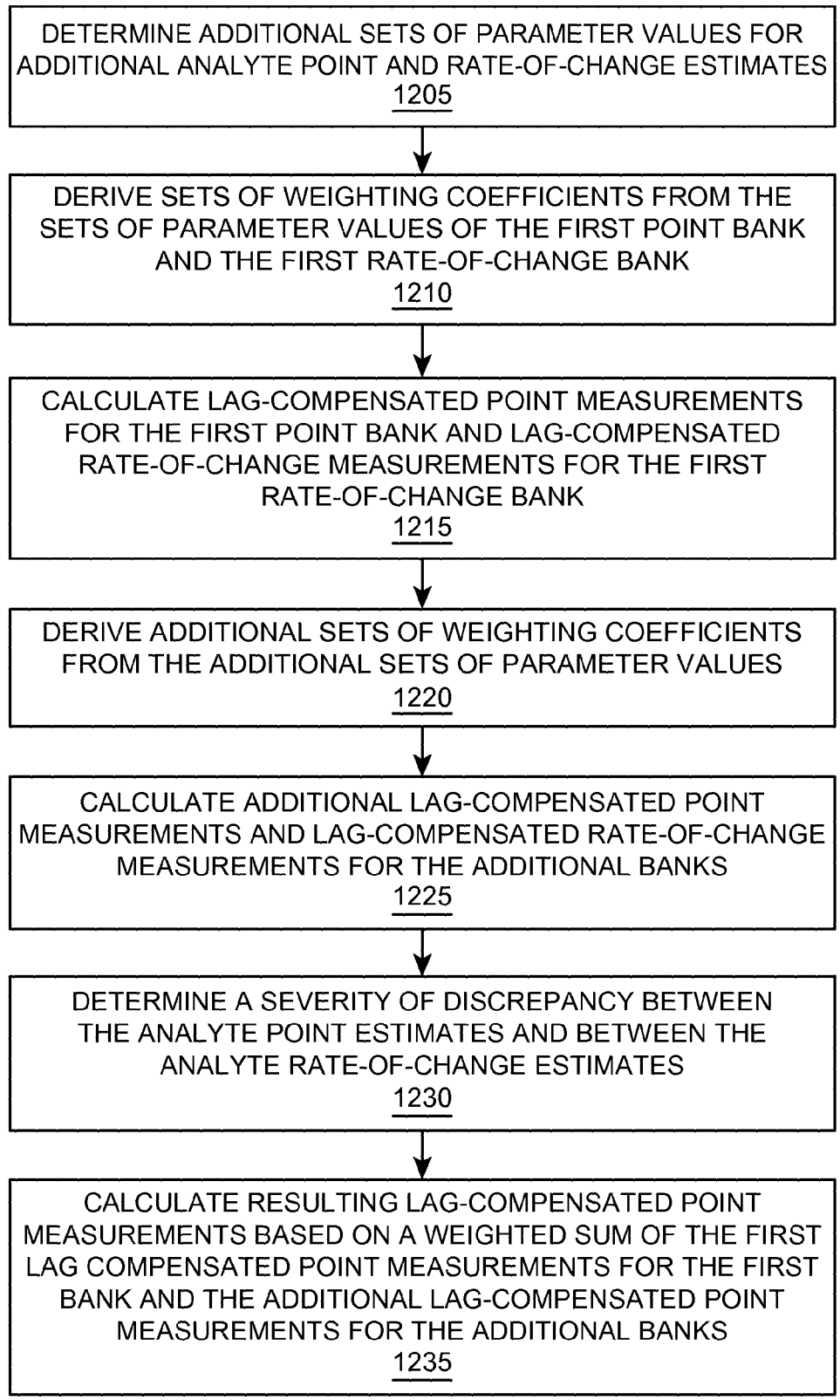
FIG. 12 illustrates a flowchart for a method of lag compensation of analyte point and rate-of-change measurements with multiple banks in each, according to one embodiment.

Furthermore, it should be appreciated that some embodiments may include additional banks in both analyte point and rate-of-change estimates. FIG. 12, for example, illustrates a flowchart for a method of lag compensation of analyte point and rate-of-change measurements with multiple banks in each, according to one embodiment. The method in FIG. 12 may be implemented, for example, with respect to the method shown in FIG. 5, and reference is made to FIG. 5. It should be appreciated, that the principles may be similarly and equally applicable to FIG. 8. It is noted that the methods shown in FIGS. 10 and 11 above, may be independently performed to provide respective outputs. For the sake of clarity and brevity, common aspects will not be described in great detail again.

At block 1205, additional sets of parameter values for additional analyte point and rate-of-change estimates (e.g., additional banks) are determined. At block 1210, sets of weighting coefficients for the first bank are derived from the first set of parameter values for the analyte point and rate-of-change estimates of the first bank (e.g., from FIG. 5).

At block 1215, lag-compensated point measurements are calculated from the uncompensated analyte measurements by applying the first sets of weighting coefficients for the analyte point and rate-of-change estimates of the first bank to corresponding uncompensated analyte measurements received at the initial reference time and the prior reference times of the first set of parameter values for the analyte point and rate-of-change estimates of the first bank (e.g., from FIG. 5).

At block 1220, additional sets of weighting coefficients are derived from the additional sets of parameter values for the analyte point and rate-of-change estimates of the additional banks. At block 1225, additional lag-compensated point measurements are calculated for the additional banks. For example, additional lag-compensated point measurements are calculated from the uncompensated analyte measurements by applying the additional sets of weighting coefficients for the first bank to corresponding uncompensated analyte measurements received at the alternate initial reference time and at the prior reference times of each of the additional sets of parameter values for the analyte point and rate-of-change estimates of the additional banks At block 1230, a severity of discrepancy is determined between the analyte point estimates, and between the analyte rate-of-change estimates. At block 1235, resulting lag-compensated point measurements are generated based on a weighted sum of the lag compensated point measurements of the first bank and the additional lag-compensated point measurements for the analyte point and rate-of-change estimates of the additional banks. The weighted sum is based on the severity of discrepancy.

Devices and Systems

Embodiments of the present disclosure relate to the continuous, periodic, and/or on demand in vivo monitoring of the level of one or more analytes using a continuous, periodic, intermittent, or on-demand analyte monitoring device or system. The system may include an analyte sensor at least a portion of which is to be positioned beneath a skin surface of a user for a period of time. Systems may include wholly implantable analyte sensors and analyte sensors in which only a portion of the sensor is positioned under the skin and a portion of the sensor resides above the skin, e.g., for contact to a sensor control unit (which may include a transmitter), a receiver/display unit, transceiver, processor, etc. The sensor may be, for example, subcutaneously positionable in a user for the continuous, periodic, or on-demand monitoring of a level of an analyte in the user's interstitial fluid.

An analyte sensor may be positioned in contact with interstitial fluid to detect the level of glucose, which detected glucose may be used to infer the glucose level in the user's bloodstream. Embodiments of the analyte sensors may be configured for monitoring the level of the analyte over a time period which may range from seconds, minutes, hours, days, weeks, to months, or longer. In one embodiment, the analyte sensors, such as glucose sensors, are capable of in vivo detection of an analyte for one hour or more, e.g., a few hours or more, e.g., a few days or more, e.g., three or more days, e.g., five days or more, e.g., seven days or more, e.g., several weeks or more, or one month or more.

As demonstrated herein, the methods of the present disclosure are useful in connection with a device that is used to measure or monitor an analyte (e.g., glucose), such as any such device described herein. These methods may also be used in connection with a device that is used to measure or monitor another analyte (e.g., ketones, ketone bodies, HbA1c, and the like), including oxygen, carbon dioxide, proteins, drugs, or another moiety of interest, for example, or any combination thereof, found in bodily fluid, including subcutaneous fluid, dermal fluid (sweat, tears, and the like), interstitial fluid, or other bodily fluid of interest, for example, or any combination thereof.

Figure 13:
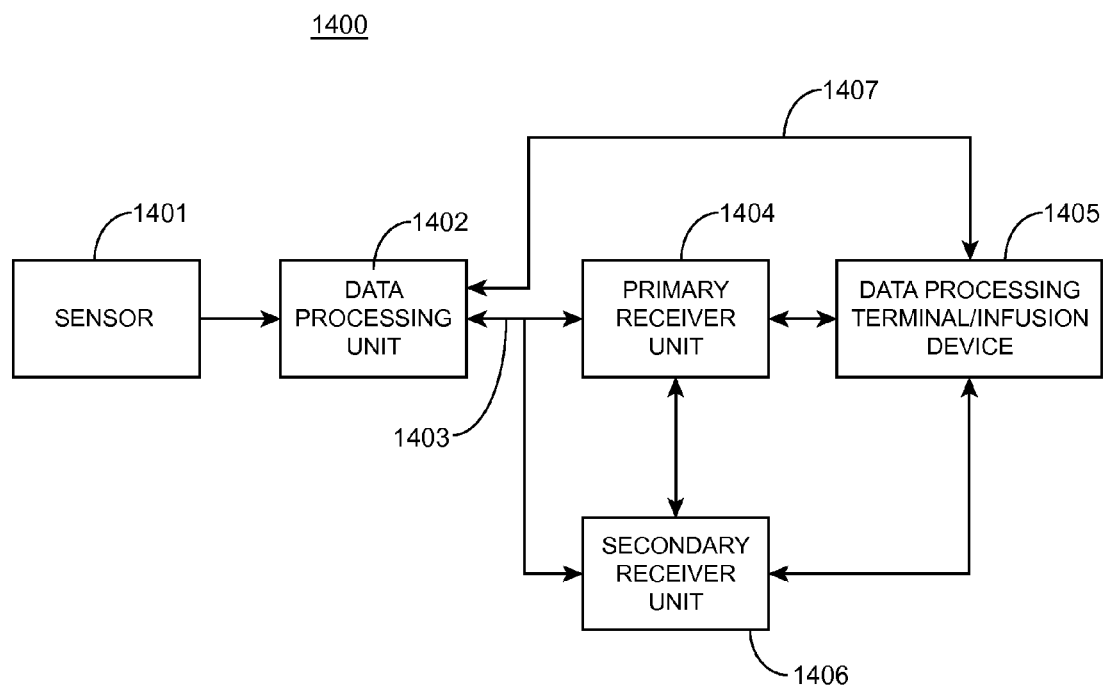
FIG. 13 shows an analyte (e.g., glucose) monitoring system, according to one embodiment.

FIG. 13 shows an analyte (e.g., glucose) monitoring system, according to one embodiment. Aspects of the subject disclosure are further described primarily with respect to glucose monitoring devices and systems, and methods of glucose detection, for convenience only and such description is in no way intended to limit the scope of the embodiments. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, glycosylated hemoglobin (HbA1c), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

The analyte monitoring system 1400 includes an analyte sensor 1401, a data processing unit 1402 connectable to the sensor 1401, and a primary receiver unit 1404. In some instances, the primary receiver unit 1404 is configured to communicate with the data processing unit 1402 via a communication link 1403. In one embodiment, the primary receiver unit 1404 may be further configured to transmit data to a data processing terminal 1405 to evaluate or otherwise process or format data received by the primary receiver unit 1404. The data processing terminal 1405 may be configured to receive data directly from the data processing unit 1402 via a communication link 1407, which may optionally be configured for bi-directional communication. Further, the data processing unit 1402 may include a transmitter or a transceiver to transmit and/or receive data to and/or from the primary receiver unit 1404 and/or the data processing terminal 1405 and/or optionally a secondary receiver unit 1406.

Also shown in FIG. 13 is an optional secondary receiver unit 1406 which is operatively coupled to the communication link 1403 and configured to receive data transmitted from the data processing unit 1402. The secondary receiver unit 1406 may be configured to communicate with the primary receiver unit 1404, as well as the data processing terminal 1405. In one embodiment, the secondary receiver unit 1406 may be configured for bi-directional wireless communication with each of the primary receiver unit 1404 and the data processing terminal 1405. As discussed in further detail below, in some instances, the secondary receiver unit 1406 may be a de-featured receiver as compared to the primary receiver unit 1404, for instance, the secondary receiver unit 1406 may include a limited or minimal number of functions and features as compared with the primary receiver unit 1404. As such, the secondary receiver unit 1406 may include a smaller (in one or more, including all, dimensions), compact housing or embodied in a device including a wrist watch, arm band, PDA, mp 3 player, cell phone, etc., for example. Alternatively, the secondary receiver unit 106 may be configured with the same or substantially similar functions and features as the primary receiver unit 1404. The secondary receiver unit 106 may include a docking portion configured to mate with a docking cradle unit for placement by, e.g., the bedside for night time monitoring, and/or a bi-directional communication device. A docking cradle may recharge a power supply.

Only one analyte sensor 1401, data processing unit 1402 and data processing terminal 1405 are shown in the embodiment of the analyte monitoring system 1400 illustrated in FIG. 13. However, it will be appreciated by one of ordinary skill in the art that the analyte monitoring system 1400 may include more than one sensor 1401 and/or more than one data processing unit 1402, and/or more than one data processing terminal 1405. Multiple sensors may be positioned in a user for analyte monitoring at the same or different times.

The analyte monitoring system 1400 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 1400. For example, unique IDs, communication channels, and the like, may be used.

In one embodiment, the sensor 1401 is physically positioned in or on the body of a user whose analyte level is being monitored. The sensor 1401 may be configured to at least periodically sample the analyte level of the user and convert the sampled analyte level into a corresponding signal for transmission by the data processing unit 1402. The data processing unit 1402 is coupleable to the sensor 1401 so that both devices are positioned in or on the user's body, with at least a portion of the analyte sensor 1401 positioned transcutaneously. The data processing unit may include a fixation element, such as an adhesive or the like, to secure it to the user's body. A mount (not shown) attachable to the user and mateable with the data processing unit 1402 may be used. For example, a mount may include an adhesive surface. The data processing unit 1402 performs data processing functions, where such functions may include, but are not limited to, filtering and encoding of data signals, each of which corresponds to a sampled analyte level of the user, for transmission to the primary receiver unit 1404 via the communication link 1403. In one embodiment, the sensor 1401 or the data processing unit 1402 or a combined sensor/data processing unit may be wholly implantable under the skin surface of the user.

In one embodiment, the primary receiver unit 1404 may include an analog interface section including an RF receiver and an antenna that is configured to communicate with the data processing unit 1402 via the communication link 1403, and a data processing section for processing the received data from the data processing unit 1402 including data decoding, error detection and correction, data clock generation, data bit recovery, etc., or any combination thereof.

The primary receiver unit 1404 in one embodiment is configured to synchronize with the data processing unit 1402 to uniquely identify the data processing unit 1402, based on, for example, an identification information of the data processing unit 1402, and thereafter, to periodically receive signals transmitted from the data processing unit 1402 associated with the monitored analyte levels detected by the sensor 1401.

The data processing terminal 1405 may include a personal computer, a portable computer including a laptop or a handheld device (e.g., a personal digital assistant (PDA), a telephone including a cellular phone (e.g., a multimedia and Internet-enabled mobile phone including an iPhone™, a Blackberry®, or similar phone), an mp 3 player (e.g., an iPOD™, etc.), a pager, and the like), and/or a drug delivery device (e.g., an infusion device), each of which may be configured for data communication with the receiver via a wired or a wireless connection. Additionally, the data processing terminal 1405 may further be connected to a data network (not shown) for storing, retrieving, updating, and/or analyzing data corresponding to the detected analyte level of the user.

The data processing terminal 1405 may include a drug delivery device (e.g., an infusion device) such as an insulin infusion pump or the like, which may be configured to administer a drug (e.g., insulin) to the user, and which may be configured to communicate with the primary receiver unit 104 for receiving, among others, the measured analyte level. Alternatively, the primary receiver unit 1404 may be configured to integrate an infusion device therein so that the primary receiver unit 1404 is configured to administer an appropriate drug (e.g., insulin) to users, for example, for administering and modifying basal profiles, as well as for determining appropriate boluses for administration based on, among others, the detected analyte levels received from the data processing unit 1402. An infusion device may be an external device or an internal device, such as a device wholly implantable in a user.

In one embodiment, the data processing terminal 1405, which may include an infusion device, e.g., an insulin pump, may be configured to receive the analyte signals from the data processing unit 1402, and thus, incorporate the functions of the primary receiver unit 1404 including data processing for managing the user's insulin therapy and analyte monitoring. In one embodiment, the communication link 1403, as well as one or more of the other communication interfaces shown in FIG. 13, may use one or more wireless communication protocols, such as, but not limited to: an RF communication protocol, an infrared communication protocol, a Bluetooth enabled communication protocol, an 802.11x wireless communication protocol, or an equivalent wireless communication protocol which would allow secure, wireless communication of several units (for example, per Health Insurance Portability and Accountability Act (HIPPA) requirements), while avoiding potential data collision and interference.

Figure 14:
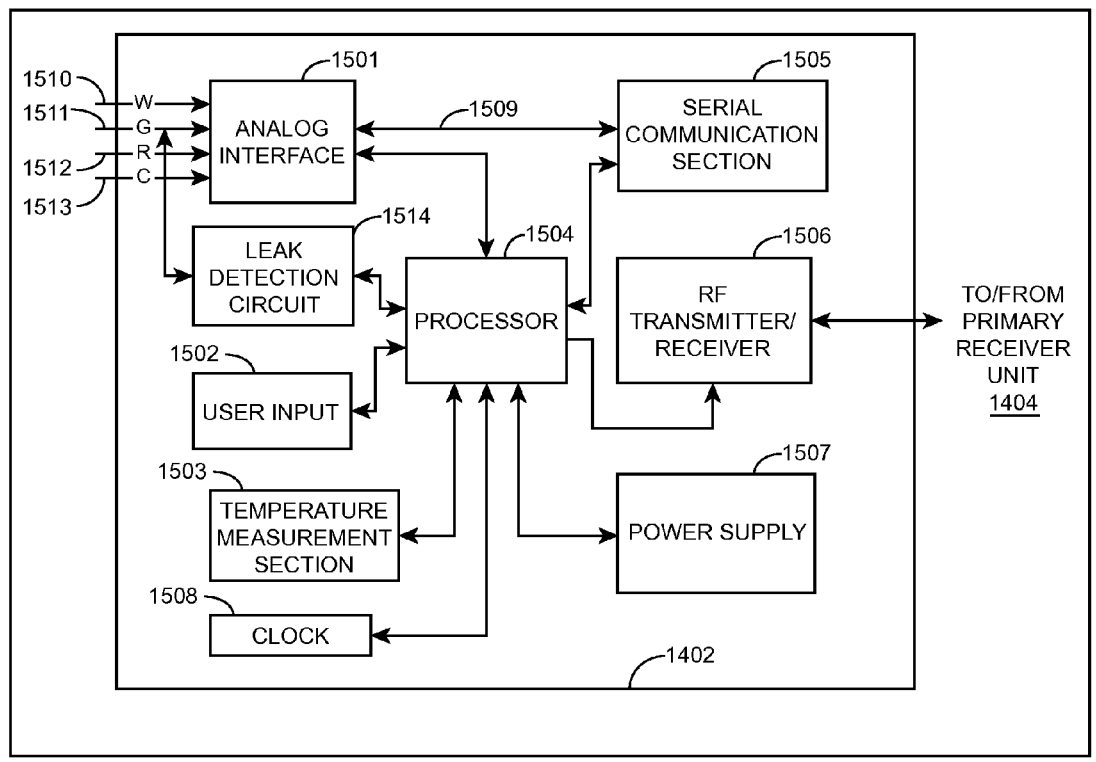
FIG. 14 is a block diagram of the data processing unit 1402 shown in FIG. 13 in accordance with one embodiment.

FIG. 14 is a block diagram of the data processing unit 1402 shown in FIG. 13 in accordance with one embodiment. Data processing unit 1402 includes an analog interface 1501 configured to communicate with the sensor 1401, a user input 1502, and a temperature measurement section 1503, each of which is operatively coupled to processor 1504 such as a central processing unit (CPU). Furthermore, unit 1402 is shown to include a serial communication section 1505, clock 1508, and an RF transmitter 1506, each of which is also operatively coupled to the processor 1504. Moreover, a power supply 1507 such as a battery is also provided in unit 1402 to provide the necessary power.

It should be appreciated that in another embodiment, the data processing unit may not include all components in the exemplary embodiment shown. User input and/or interface components may be included or a data processing unit may be free of user input and/or interface components. In one embodiment, one or more application-specific integrated circuits (ASIC) may be used to implement one or more functions or routines associated with the operations of the data processing unit (and/or receiver unit) using for example one or more state machines and buffers.

The analyte sensor 1401 is shown including four contacts, three of which are electrodes: a work electrode (W) 1510, a reference electrode (R) 1512, and a counter electrode (C) 1513, each operatively coupled to the analog interface 1501 of the data processing unit 1402. This embodiment also shows an optional guard contact (G) 1511. Fewer or greater electrodes may be employed. For example, the counter and reference electrode functions may be served by a single counter/reference electrode. In some cases, there may be more than one working electrode and/or reference electrode and/or counter electrode, etc.

Figure 15:
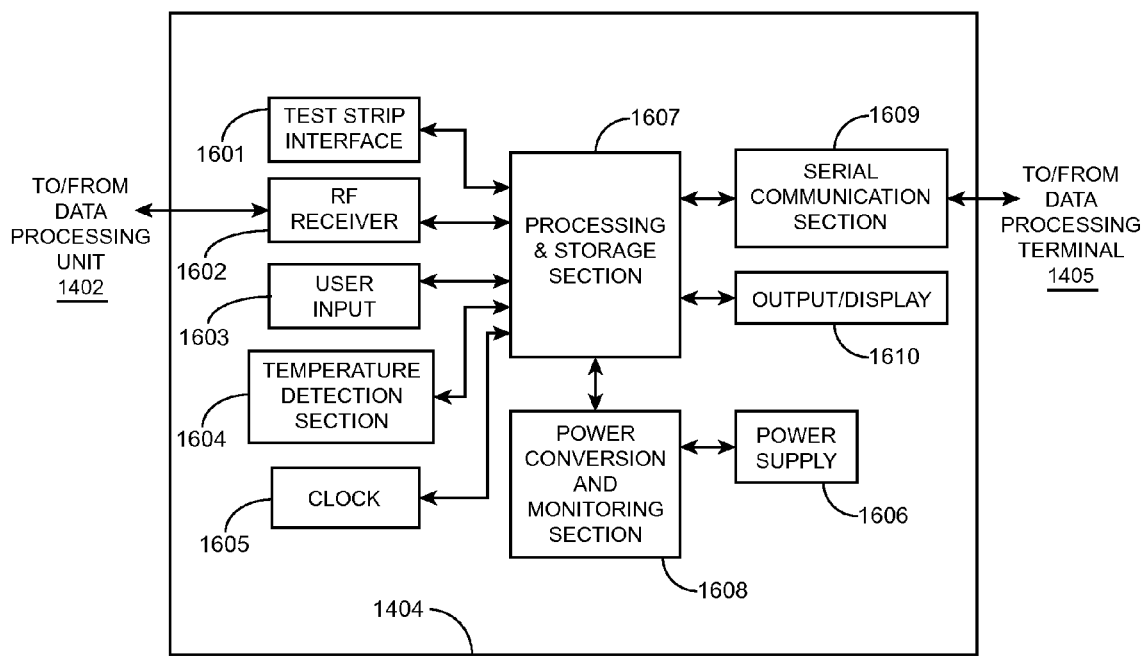
FIG. 15 is a block diagram of an embodiment of a receiver/monitor unit such as the primary receiver unit 1404 of the analyte monitoring system shown in FIG. 13.

FIG. 15 is a block diagram of an embodiment of a receiver/monitor unit such as the primary receiver unit 1404 of the analyte monitoring system shown in FIG. 13. The primary receiver unit 1404 includes one or more of: a test strip interface 1601, an RF receiver 1602, a user input 1603, an optional temperature detection section 1604, and a clock 1605, each of which is operatively coupled to a processing and storage section 1607. The primary receiver unit 1404 also includes a power supply 1606 operatively coupled to a power conversion and monitoring section 1608. Further, the power conversion and monitoring section 1608 is also coupled to the processing and storage section 1607. Moreover, also shown are a receiver serial communication section 1609, and an output 1610, each operatively coupled to the processing and storage section 1607. The primary receiver unit 1404 may include user input and/or interface components or may be free of user input and/or interface components.

In one embodiment, the test strip interface 1601 includes an analyte testing portion (e.g., a glucose level testing portion) to receive a blood (or other body fluid sample) analyte test or information related thereto. For example, the test strip interface 1601 may include a test strip port to receive a test strip (e.g., a glucose test strip). The device may determine the analyte level of the test strip, and optionally display (or otherwise notice) the analyte level on the output 1610 of the primary receiver unit 1404. Any suitable test strip may be employed, e.g., test strips that only require a very small amount (e.g., 3 microliters or less, e.g., 1 microliter or less, e.g., 0.5 microliters or less, e.g., 0.1 microliters or less), of applied sample to the strip in order to obtain accurate glucose information. Embodiments of test strips include, e.g., Freestyle® blood glucose test strips from Abbott Diabetes Care, Inc. (Alameda, Calif.). Glucose information obtained by an in vitro glucose testing device may be used for a variety of purposes, computations, etc. For example, the information may be used to calibrate sensor 1401, confirm results of sensor 1401 to increase the confidence thereof (e.g., in instances in which information obtained by sensor 1401 is employed in therapy related decisions), etc.

In further embodiments, the data processing unit 1402 and/or the primary receiver unit 1404 and/or the secondary receiver unit 1406, and/or the data processing terminal/infusion device 1405 may be configured to receive the analyte value wirelessly over a communication link from, for example, a blood glucose meter. In further embodiments, a user manipulating or using the analyte monitoring system 1400 (FIG. 13) may manually input the analyte value using, for example, a user interface (for example, a keyboard, keypad, voice commands, and the like) incorporated in one or more of the data processing unit 1402, the primary receiver unit 1404, secondary receiver unit 1406, or the data processing terminal/infusion device 1405.

Additional detailed descriptions are provided in U.S. Pat. Nos. 5,262,035; 5,264,104; 5,262,305; 5,320,715; 5,593,852; 6,175,752; 6,650,471; 6,746, 582, and 7,811,231, each of which is incorporated herein by reference in their entirety.

In certain embodiments, the sensing elements include one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes including ferrocene. Examples of inorganic redox species are hexacyanoferrate (III), ruthenium hexamine, etc.

In certain embodiments, electron transfer agents have structures or charges which prevent or substantially reduce the diffusional loss (e.g., non-leachable) of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

Embodiments of polymeric electron transfer agents may contain a redox species covalently bound in a polymeric composition. An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer including quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, including 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing elements may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, including a glucose oxidase, glucose dehydrogenase (e.g., pyrroloquinoline quinone (PQQ), dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent, which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

In certain embodiments, the sensor works at a low oxidizing potential, e.g., a potential of about +40 mV vs. Ag/AgCl. This sensing elements use, for example, an osmium (Os)-based mediator constructed for low potential operation. Accordingly, in certain embodiments the sensing elements are redox active components that include: (1) osmium-based mediator molecules that include (bidente) ligands, and (2) glucose oxidase enzyme molecules. These two constituents are combined together in the sensing elements of the sensor.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may provide many functions, e.g., biocompatibility and/or interferent-eliminating functions, etc. In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

In some instances, the analyte monitoring device includes processing circuitry that is able to determine a level of the analyte and activate an alarm system if the analyte level exceeds a threshold. The analyte monitoring device, in these embodiments, has an alarm system and may also include a display, such as an LCD or LED display. An alarm may also be activated if the sensor readings indicate a value that is beyond a measurement range of the sensor. For glucose, the physiologically relevant measurement range is typically 30-400 mg/dL, including 40-300 mg/dL and 50-250 mg/dL, of glucose in the interstitial fluid. The alarm system may also, or alternatively, be activated when the rate-of-change or acceleration of the rate-of-change in analyte level increase or decrease reaches or exceeds a threshold rate or acceleration. For example, in the case of a subcutaneous glucose monitor, the alarm system might be activated if the rate-of-change in glucose concentration exceeds a threshold value which might indicate that a hyperglycemic or hypoglycemic condition is likely to occur. A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Drug Delivery System

The present disclosure may also relate to sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

Each of the various references, presentations, publications, provisional and/or non-provisional U.S. patent applications, U.S. patents, non-U.S. patent applications, and/or non-U.S. patents that have been identified herein, is incorporated herein by reference in its entirety.

Other embodiments and modifications within the scope of the present disclosure will be apparent to those skilled in the relevant art. Various modifications, processes, as well as numerous structures to which the embodiments of the present disclosure may be applicable will be readily apparent to those of skill in the art to which the present disclosure is directed upon review of the specification. Various aspects and features of the present disclosure may have been explained or described in relation to understandings, beliefs, theories, underlying assumptions, and/or working or prophetic examples, although it will be understood that the present disclosure is not bound to any particular understanding, belief, theory, underlying assumption, and/or working or prophetic example. Although various aspects and features of the present disclosure may have been described largely with respect to applications, or more specifically, medical applications, involving diabetic humans, it will be understood that such aspects and features also relate to any of a variety of applications involving non-diabetic humans and any and all other animals. Further, although various aspects and features of the present disclosure may have been described largely with respect to applications involving partially implanted sensors, such as transcutaneous or subcutaneous sensors, it will be understood that such aspects and features also relate to any of a variety of sensors that are suitable for use in connection with the body of an animal or a human, such as those suitable for use as fully implanted in the body of an animal or a human. Finally, although the various aspects and features of the present disclosure have been described with respect to various embodiments and specific examples herein, all of which may be made or carried out conventionally, it will be understood that the invention is entitled to protection within the full scope of the appended claims.

Additional Example Embodiments

As stated above, in some aspects of the present disclosure, methods of lag compensation for analyte point measurements are provided. The methods include receiving reference analyte measurements; and determining a first set of parameter values for an analyte point estimate based on the reference analyte measurements. The analyte point estimate is based on a sum of an analyte point and a sum of a plurality of scaled rates-of-changes. The analyte point corresponds to measurements at an initial reference time. The rates-of-changes include a first rate-of-change from the initial reference time to a first prior reference time, and a second rate-of-change from the initial reference time to a second prior reference time.

In one embodiment, the first set of parameter values includes a first scalar of the first rate-of-change, the first prior reference time, a second scalar of the second rate-of-change, and the second prior reference time.

In one embodiment, the determining of the first set of parameter values includes calculating error metrics for a plurality of combinations of values as parameters in the analyte point estimate, and selecting the first set of parameter values based on the calculated error metrics. In some instances, the error metrics are generated by calculating a sum-of-squared-errors. In some instances, the first set of parameter values is associated with a smallest error metric calculated.

In one embodiment, the method includes receiving a series of uncompensated analyte measurements, deriving a first set of weighting coefficients from the first set of parameter values, and calculating lag-compensated point measurements from the uncompensated analyte measurements. The lag-compensated point measurements are calculated by applying the first set of weighting coefficients to corresponding uncompensated analyte measurements received at the initial reference time, at the first prior reference time, and at the second prior reference time of the first parameter values.

In some embodiments, a second filter is implemented. In one embodiment, the method includes determining a second set of parameter values for the analyte point estimate based on the reference analyte measurements. The first set and the second set of parameter values point to different sets of prior reference times. In one embodiment, the determining of the first set and the second set of parameter values includes calculating error metrics for a plurality of combinations of values as parameters in the analyte point estimate, and selecting the first set and the second set of parameter values based on the calculated error metrics. In some instances, the error metrics are generated by calculating a sum-of-squared-errors.

In one embodiment, the method includes receiving a series of uncompensated analyte measurements, deriving a first set of weighting coefficients from the first set of parameter values, deriving a second set of weighting coefficients from the second set of parameter values, and calculating lag-compensated point measurements by averaging a first output and a second output. The first output is generated by applying the first set of weighting coefficients to corresponding uncompensated analyte measurements received at the initial reference time, at the first prior reference time, and at the second prior reference time of the first set of parameter values. The second output is generated by applying the second set of weighting coefficients to corresponding uncompensated analyte measurements received at the initial reference time, at the first prior reference time, and at the second prior reference time of the second set of parameter values.

In one embodiment, the method includes receiving a series of uncompensated analyte measurements, deriving a first set of weighting coefficients from the first set of parameter values, and deriving a second set of weighting coefficients from the second set of parameter values. When valid data is present at the first prior reference time and the second prior reference time for the first set of parameter values, lag-compensated point measurements are calculated from the uncompensated analyte measurements by applying the first set of weighting coefficients to corresponding uncompensated analyte measurements received at the initial reference time, at the first prior reference time, and at the second prior reference time of the first set of parameter values. When valid data is present at the first prior reference time and the second prior reference time for the second set of parameter values and not the first set of parameter values, lag-compensated point measurements are calculated from the uncompensated analyte measurements by applying the second set of weighting coefficients to corresponding uncompensated analyte measurements received at the initial reference time, at the first prior reference time, and at the second prior reference time of the second set of parameter values.

In some embodiments, a third filter is implemented. In one embodiment, the method includes determining a third set of parameter values for the analyte point estimate based on the reference analyte measurements. The first, second, and third sets of parameter values point to different sets of prior reference times. In one embodiment, the determining of the first set, the second set, and the third set of parameter values includes calculating error metrics for a plurality of combinations of values as parameters in the analyte point estimate, and selecting the first set, the second set, and the third set of parameter values based on the calculated error metrics. In some instances, the error metrics are generated by calculating a sum-of-squared-errors. The first set of parameter values is associated with a smaller calculated error metric than the second set of parameter values, and the second set of parameter values is associated with a smaller calculated error metric than the third set of parameter values.

In one embodiment, the method includes receiving a series of uncompensated analyte measurements, deriving a first set of weighting coefficients from the first set of parameter values, deriving a second set of weighting coefficients from the second set of parameter values, deriving a third set of weighting coefficients from the third set of parameter values, and calculating lag-compensated point measurements by averaging available outputs. The available outputs are generated by applying the first, second, and/or third sets of weighting coefficients to uncompensated analyte measurements received at the initial reference time and prior reference times of respective first, second, and/or third sets of parameter values which have valid data present.

In one embodiment, the method includes receiving a series of uncompensated analyte measurements, deriving a first set of weighting coefficients from the first set of parameter values, deriving a second set of weighting coefficients from the second set of parameter values, and deriving a third set of weighting coefficients from the third set of parameter values. When valid data is present at the first prior reference time and the second prior reference time for the first set of parameter values, lag-compensated point measurements are calculated from the uncompensated analyte measurements by applying the first set of weighting coefficients to corresponding uncompensated analyte measurements received at the initial reference time, at the first prior reference time, and at the second prior reference time for the first set of parameter values. When valid data is present at the first prior reference time and the second prior reference time of the second set of parameter values and not the first set of parameter values, lag-compensated point measurements are calculated from the uncompensated analyte measurements by applying the second set of weighting coefficients to corresponding uncompensated analyte measurements received at the initial reference time, at the first prior reference time, and at the second prior reference time of the second set of parameter values. When valid data is present at the first prior reference time and the second prior reference time of the third set of parameter values and not the first set or the second set of parameter values, lag-compensated point measurements are calculated from the uncompensated analyte measurements by applying the third set of weighting coefficients to corresponding uncompensated analyte measurements received at the initial reference time, at the first prior reference time, and at the second prior reference time of the third set of parameter values.

In some embodiments, four or more filters may be implemented. In one embodiment, the method includes determining three or more additional sets of parameter values for the analyte point estimate based on the reference analyte measurements. The three or more additional sets of parameter values point to different sets of prior reference times.

In some embodiments, a second bank is implemented. In one embodiment, the method includes determining a fourth set of parameter values for a second analyte point estimate. The second analyte point estimate is based on a sum of an analyte point and a sum of a plurality of scaled rates-of-changes. Further, the analyte point corresponds to measurements at an alternate initial reference time, wherein the alternate initial reference time is prior to the initial reference time by a time delay. The rates-of-changes include a third rate-of-change from the alternate initial reference time to a fourth prior reference time with respect to the alternate initial reference time, and a second rate-of-change from the alternate initial reference time to a fifth prior reference time with respect to the alternate initial reference time. In some instances, the time delay is predetermined based on a projected duration of artifacts.

In one embodiment, the method includes deriving a first set of weighting coefficients from the first set of parameter values; calculating first lag-compensated point measurements from the uncompensated analyte measurements by applying the first set of weighting coefficients to corresponding uncompensated analyte measurements received at the initial reference time, at the first prior reference time, and at the second prior reference time of the first set of parameter values; deriving a fourth set of weighting coefficients from the fourth set of parameter values; calculating second lag-compensated point measurements from the uncompensated analyte measurements by applying the fourth set of weighting coefficients to corresponding uncompensated analyte measurements received at the alternate initial reference time, at the fourth prior reference time, and at the fifth prior reference time of the fourth set of parameter values; determining a severity of discrepancy between the first and the second analyte point estimates; and generating resulting lag-compensated point measurements based on a weighted sum of the first lag compensated point measurements and the second lag-compensated point measurements, wherein the weighted sum is based on the severity of discrepancy.

In some embodiments, three or more banks may be implemented. In one embodiment, the method includes determining additional sets of parameter values for two or more additional analyte point estimates. The two or more additional analyte point estimates are based on sums of an analyte point and sums of a plurality of scaled rates-of-changes. The analyte point corresponds to measurements at an alternate initial reference time, wherein the alternate initial reference time is prior to the initial reference time by a time delay. Further, the plurality of scaled rates-of-changes for each of the two or more additional analyte point estimates are from the alternate initial reference time to fourth and fifth prior reference times with respect to the alternate initial reference time. Each set of reference times for the analyte point estimate and the additional analyte point estimates is unique as a whole. In some instances, the time delay is predetermined based on a projected duration of artifacts.

In one embodiment, the method includes deriving a first set of weighting coefficients from the first set of parameter values; calculating first lag-compensated point measurements from the uncompensated analyte measurements by applying the first set of weighting coefficients to corresponding uncompensated analyte measurements received at the initial reference time, at the first prior reference time, and at the second prior reference time of the first set of parameter values; deriving additional sets of weighting coefficients from the additional sets of parameter values; calculating additional lag-compensated point measurements from the uncompensated analyte measurements by applying the additional sets of weighting coefficients to corresponding uncompensated analyte measurements received at the alternate initial reference time, and at the fourth and fifth prior reference times of each of the additional sets of parameter values; determining a severity of discrepancy between the analyte point estimates; and generating resulting lag-compensated point measurements based on a weighted sum of the first lag compensated point measurements and the additional lag-compensated point measurements, wherein the weighted sum is based on the severity of discrepancy.

In some embodiments, the analyte point estimate may include three or more rates-of-changes. In one embodiment, the method includes one or more additional rates-of-changes from the initial reference time to additional prior reference times. In some instances, the first set of parameter values include the first scalar of the first rate-of-change, the first prior reference time, the second scalar of the second rate-of-change, the second prior reference time, additional scalars for the additional rates-of-changes, and each of the additional prior reference times.

In one embodiment, the method includes receiving a series of uncompensated analyte measurements, deriving weighting coefficients from the first set of parameter values, and calculating lag-compensated point measurements from the uncompensated analyte measurements. The lag-compensated point measurements are calculated by applying the weighting coefficients to corresponding uncompensated analyte measurements received at the initial reference time, at the first prior reference time, at the second prior reference time, and at each of the additional prior reference times.

As stated above, in some aspects of the present disclosure, articles of manufacture for lag compensation of analyte point measurements are provided. The articles of manufacture include a machine-readable medium having machine-executable instructions stored thereon for lag compensation of analyte measurements. The instructions include instructions for receiving reference analyte measurements, and instructions for determining a first set of parameter values for an analyte point estimate based on the reference analyte measurements. The analyte point estimate is based on a sum of an analyte point and a sum of a plurality of scaled rates-of-changes. The analyte point corresponds to measurements at an initial reference time. The rates-of-changes include a first rate-of-change from the initial reference time to a first prior reference time, and a second rate-of-change from the initial reference time to a second prior reference time.

It should be appreciated that similar embodiments to those described above for the methods of lag compensation for analyte point measurements are applicable to the articles of manufacture as well.

In some aspects of the present disclosure, methods of lag compensation for analyte rate-of-change measurements are provided. The methods include receiving reference analyte measurements, and determining a first set of parameter values for an analyte rate-of-change estimate based on the reference analyte measurements. The analyte rate-of-change estimate is based on a sum of a plurality of scaled rates-of-changes. The rates-of-changes include a first rate-of-change from an initial reference time to a first prior reference time, and a second rate-of-change from the initial reference time to a second prior reference time.

In one embodiment, the method includes receiving reference analyte measurements, and determining a first set of parameter values for an analyte rate-of-change estimate based on the reference analyte measurements. The analyte rate-of-change estimate is based on a sum of a plurality of scaled rates-of-changes. The rates-of-changes include a first rate-of-change from an initial reference time to a first prior reference time, and a second rate-of-change from the initial reference time to a second prior reference time.

In one embodiment, the parameter values include a first scalar of the first rate-of-change, the first prior reference time, a second scalar of the second rate-of-change, and the second prior reference time.

In one embodiment, the determining of the first set of parameter values includes calculating error metrics for a plurality of combinations of values as parameters in the analyte rate-of-change estimate, and selecting the first set of parameter values based on the calculated error metrics. In some instances, the error metrics are generated by calculating a sum-of-squared-errors. In some instances, the first set of parameter values is associated with a smallest error metric calculated.

In one embodiment, the method includes receiving a series of uncompensated analyte measurements, deriving a first set of weighting coefficients from the first set of parameter values, and calculating lag-compensated rate-of-change measurements from the uncompensated analyte measurements. The lag-compensated rate-of-change measurements are calculated by applying the first set of weighting coefficients to corresponding uncompensated analyte measurements received at the initial reference time, at the first prior reference time, and at the second prior reference time of the first set of parameter values.

In some embodiments, a second filter may be implemented. In one embodiment, the method includes determining a second set of parameter values for the analyte rate-of-change estimate based on the reference analyte measurements. The first set and the second set of parameter values point to different sets of prior reference times.

In one embodiment, the determining of the first set and the second set of parameter values includes calculating error metrics for a plurality of combinations of values as parameters in the analyte rate-of-change estimate, and selecting the first set and the second set of parameter values based on the calculated error metrics. In some instances, the error metrics are generated by calculating a sum-of-squared-errors.

In one embodiment, the method includes receiving a series of uncompensated analyte measurements, deriving a first set of weighting coefficients from the first set of parameter values, deriving a second set of weighting coefficients from the second set of parameter values, and calculating lag-compensated rate-of-change measurements by averaging a first output and a second output. The first output is generated by applying the first set of weighting coefficients to corresponding uncompensated analyte measurements received at the initial reference time, at the first prior reference time, and at the second prior reference time of the first set of parameter values. Further, the second output is generated by applying the second set of weighting coefficients to corresponding uncompensated analyte measurements received at the initial reference time, at the first prior reference time, and at the second prior reference time of the second set of parameter values.

In one embodiment, the method includes receiving a series of uncompensated analyte measurements, deriving a first set of weighting coefficients from the first set of parameter values, and deriving a second set of weighting coefficients from the second set of parameter values. When valid data is present at the first prior reference time and the second prior reference time of the first set of parameter values, lag-compensated rate-of-change measurements are calculated from the uncompensated analyte measurements by applying the first set of weighting coefficients to corresponding uncompensated analyte measurements received at the initial reference time, at the first prior reference time, and at the second prior reference time of the first set of parameter values. When valid data is present at the first prior reference time and the second prior reference time of the second set of parameter values and not the first set of parameter values, lag-compensated rate-of-change measurements are calculated from the uncompensated analyte measurements by applying the second set of weighting coefficients to corresponding uncompensated analyte measurements received at the initial reference time, at the first prior reference time, and at the second prior reference time of the second set of parameter values.

In some embodiments, a third filter may be implemented. In one embodiment, the method includes determining a third set of parameter values for the analyte rate-of-change estimate based on the reference analyte measurements. The first set, second set, and third set of parameter values point to different sets of reference times.

In one embodiment, the determining of the first set, the second set, and the third set of parameter values includes calculating error metrics for a plurality of combinations of values as parameters in the analyte rate-of-change estimate, and selecting the first set, the second set, and the third set of parameter values based on the calculated error metrics. In some instances, the error metrics are generated by calculating a sum-of-squared-errors. The first set of parameter values is associated with a smaller calculated error metric than the second set of parameter values, and the second set of parameter values is associated with a smaller calculated error metric than the third set of parameter values.

In one embodiment, the method includes receiving a series of uncompensated analyte measurements, deriving a first set of weighting coefficients from the first set of parameter values, deriving a second set of weighting coefficients from the second set of parameter values, deriving a third set of weighting coefficients from the third set of parameter values, and calculating lag-compensated rate-of-change measurements by averaging available outputs, wherein the available outputs are generated by applying the first, second, and/or third sets of weighting coefficients to uncompensated analyte measurements received at the initial reference time and prior reference times of respective first, second, and/or third sets of parameter values which have valid data present.

In one embodiment, the method includes receiving a series of uncompensated analyte measurements, deriving a first set of weighting coefficients from the first set of parameter values, deriving a second set of weighting coefficients from the second set of parameter values, and deriving a third set of weighting coefficients from the third set of parameter values. When valid data is present at the first prior reference time and the second prior reference time of the first set of parameter values, lag-compensated rate-of-change measurements are calculated from the uncompensated analyte measurements by applying the first set of weighting coefficients to corresponding uncompensated analyte measurements received at the initial reference time, at the first prior reference time, and at the second prior reference time of the first set of parameter values. When valid data is present at the first prior reference time and the second prior reference time of the second set of parameter values and not the first set of parameter values, lag-compensated rate-of-change measurements are calculated from the uncompensated analyte measurements by applying the second set of weighting coefficients to corresponding uncompensated analyte measurements received at the initial reference time, at the first prior reference time, and at the second prior reference time of the second set of parameter values. When valid data is present at the first prior reference time and the second prior reference time of the third set of parameter values and not the first set or the second set of parameter values, lag-compensated rate-of-change measurements are calculated from the uncompensated analyte measurements by applying the third set of weighting coefficients to corresponding uncompensated analyte measurements received at the initial reference time, at the first prior reference time, and at the second prior reference time of the third set of parameter values.

In some embodiments, four or more filters may be implemented. In one embodiment, the method includes determining three or more additional sets of parameter values for the analyte rate-of-change estimate based on the reference analyte measurements. The three or more additional sets of parameter values point to different sets of prior reference times.

In some embodiments, a second bank may be implemented. In one embodiment, the method includes determining a fourth set of parameter values for a second analyte rate-of-change estimate. The second analyte rate-of-change estimate is based on a sum of a plurality of scaled rates-of-changes. The rates-of-changes include a third rate-of-change from an alternate initial reference time to a fourth prior reference time with respect to the alternate initial reference time; and a fourth rate-of-change from the alternate initial reference time to a fifth prior reference time with respect to the alternate initial reference time. The alternate initial reference time is prior to the initial reference time by a time delay. In some instances, the time delay is predetermined based on a projected duration of artifacts.

In one embodiment, the method includes deriving a first set of weighting coefficients from the first set of parameter values; calculating first lag-compensated rate-of-change measurements from the uncompensated analyte measurements by applying the first set of weighting coefficients to corresponding uncompensated analyte measurements received at the initial reference time, at the first prior reference time, and at the second prior reference time of the first set of parameter values; deriving a fourth set of weighting coefficients from the fourth set of parameter values; calculating second lag-compensated rate-of-change measurements from the uncompensated analyte measurements by applying the fourth set of weighting coefficients to corresponding uncompensated analyte measurements received at the alternate initial reference time, at the fourth prior reference time, and at the fifth prior reference time of the fourth set of parameter values; determining a severity of discrepancy between the first and the second analyte rate-of-change estimates; generating resulting lag-compensated rate-of-change measurements based on a weighted sum of the first lag compensated rate-of-change measurements and the second lag-compensated rate-of-change measurements, wherein the weighted sum is based on the severity of discrepancy.

In some embodiments, three or more banks are implemented. In one embodiment, the method includes determining additional sets of parameter values for two or more additional analyte rate-of-change estimates. The two or more additional analyte rate-of-change estimates are based on sums of a plurality of scaled rates-of-changes. The plurality of scaled rates-of-changes for each of the two or more additional analyte rate-of-change estimates are from an alternate initial reference time to fourth and fifth prior reference times with respect to the alternate initial reference time, wherein each set of reference times for the analyte rate-of-change estimate and the additional analyte rate-of-change estimates is unique as a whole. The alternate initial reference time is prior to the initial reference time by a time delay. In some instances, the time delay is predetermined based on a projected duration of artifacts.

In one embodiment, the method includes deriving a first set of weighting coefficients from the first set of parameter values; calculating first lag-compensated rate-of-change measurements from the uncompensated analyte measurements by applying the first set of weighting coefficients to corresponding uncompensated analyte measurements received at the initial reference time, at the first prior reference time, and at the second prior reference time of the first set of parameter values; deriving additional sets of weighting coefficients from the additional sets of parameter values; calculating additional lag-compensated rate-of-change measurements from the uncompensated analyte measurements by applying the additional sets of weighting coefficients to corresponding uncompensated analyte measurements received at the alternate initial reference time, and at the fourth and fifth prior reference times of each of the additional sets of parameter values; determining a severity of discrepancy between the analyte rate-of-change estimates; and generating resulting lag-compensated rate-of-change measurements based on a weighted sum of the first lag compensated output and the additional lag-compensated outputs, wherein the weighted sum is based on the severity of discrepancy.

In some embodiments, the analyte rate-of-change estimate includes three or more rates-of-changes. In one embodiment, the method includes one or more additional rates-of-changes from the initial reference time to additional prior reference times.

In one embodiment, the first set of parameter values include the first scalar of the first rate-of-change, the first prior reference time, the second scalar of the second rate-of-change, the second prior reference time, additional scalars for the additional rates-of-changes, and each of the additional prior reference times.

In one embodiment, the method includes receiving a series of uncompensated analyte measurements, deriving weighting coefficients from the first set of parameter values, and calculating lag-compensated rate-of-change measurements from the uncompensated analyte measurements. The lag-compensated rate-of-change measurements are calculated by applying the weighting coefficients to corresponding uncompensated analyte measurements received at the initial reference time, at the first prior reference time, at the second prior reference time, and at each of the additional prior reference times.

As stated above, in some aspects of the present disclosure, articles of manufacture for lag compensation of analyte rate-of-change measurements are provided. The articles of manufacture include a machine-readable medium having machine-executable instructions stored thereon for lag compensation of analyte measurements. The instructions include instructions for receiving reference analyte measurements, and instructions for determining a first set of parameter values for an analyte rate-of-change estimate based on the reference analyte measurements. The analyte rate-of-change estimate is based on a sum of a plurality of scaled rates-of-changes. The rates-of-changes include a first rate-of-change from an initial reference time to a first prior reference time, and a second rate-of-change from the initial reference time to a second prior reference time.

It should be appreciated that similar embodiments to those described above for the methods of lag compensation for analyte rate-of-change measurements are applicable to articles of manufacture as well.

In some aspects of the present disclosure, methods of lag compensation for analyte point measurements and analyte rate-of-change measurements are provided. The methods include receiving reference analyte measurements, and determining a first set of parameter values for an analyte point estimate based on the reference analyte measurements. The analyte point estimate is based on a sum of an analyte point and a sum of a first plurality of scaled rates-of-changes. The analyte point corresponds to measurements at an initial reference time. The rates-of-changes of the first plurality include a first rate-of-change from the initial reference time to a first prior reference time, and a second rate-of-change from the initial reference time to a second prior reference time. The methods also include determining a second set of parameter values for an analyte rate-of-change estimate based on the reference analyte measurements. The analyte rate-of-change estimate is based on the sum of a second plurality of scaled rates-of-changes. The rates-of-changes of the second plurality include a third rate-of-change from an initial reference time to a third prior reference time, and a fourth rate-of-change from the initial reference time to a fourth prior reference time.

In one embodiment, the method includes receiving reference analyte measurements, and determining a first set of parameter values for an analyte point estimate based on the reference analyte measurements. The analyte point estimate is based on a sum of an analyte point, and a sum of a first plurality of scaled rates-of-changes, The analyte point corresponds to measurements at an initial reference time. The rates-of-changes of the first plurality include a first rate-of-change from the initial reference time to a first prior reference time, and a second rate-of-change from the initial reference time to a second prior reference time. Furthermore, the method includes determining a second set of parameter values for an analyte rate-of-change estimate based on the reference analyte measurements. The analyte rate-of-change estimate is based on the sum of a second plurality of scaled rates-of-changes. The rates-of-changes of the second plurality include a third rate-of-change from an initial reference time to a third prior reference time, and a fourth rate-of-change from the initial reference time to a fourth prior reference time.

In one embodiment, the first prior reference time is equal to the third prior reference time, and the second prior reference time is equal to the fourth prior reference time.

In one embodiment, the first set of parameter values for the analyte point estimate includes a first scalar of the first rate-of-change, the first prior reference time, a second scalar of the second rate-of-change, and the second prior reference time. Further, the second set of parameter values for the analyte rate-of-change estimate includes a third scalar of the third rate-of-change, the third prior reference time, a fourth scalar of the fourth rate-of-change, and the fourth prior reference time.

In one embodiment, the determining of the first set of parameter values and the determining of the second set of parameter values includes calculating error metrics for a plurality of combinations of values as parameters in the analyte point estimate and the analyte rate-of-change estimate, and selecting the first set of parameter values and second set of parameter values based on the calculated error metrics. In some instances, the error metrics are generated by calculating a sum-of-squared-errors. In some instances, the first set of parameter values and second set of parameter values are associated with a smallest error metric calculated.

In one embodiment, the method includes receiving a series of uncompensated analyte measurements; deriving a first set of weighting coefficients from the first set of parameter values; deriving a second set of weighting coefficients from the second set of parameter values; and calculating lag-compensated point measurements from the uncompensated analyte measurements, wherein the lag-compensated point measurements are calculated by applying the first set of weighting coefficients to corresponding uncompensated analyte measurements received at the initial reference time, at the first prior reference time, and at the second prior reference time of the first set of parameter values; and calculating lag-compensated rate-of-change measurements from the uncompensated analyte measurements, wherein the lag-compensated rate-of-change measurements are calculated by applying the second set of weighting coefficients to corresponding uncompensated analyte measurements received at the initial reference time, at the third prior reference time, and at the fourth prior reference time of the second set of parameter values.

In some embodiments, a second filter is implemented. In one embodiment, the method includes determining a third set of parameter values for the analyte point estimate based on the reference analyte measurements. The first set and the third set of parameter values of the analyte point estimate point to different sets of prior reference times. The method further includes determining a fourth set of parameter values for the analyte rate-of-change estimate based on the reference analyte measurements. The second set and the fourth set of parameter values of the analyte rate-of-change estimate point to different sets of prior reference times.

In one embodiment, the method includes determining of the first set, second set, third set, and fourth set of parameter values includes calculating error metrics for a plurality of combinations of values as parameters in the analyte point estimates and analyte rate-of-change estimates, and selecting the first set, second set, third set, and fourth set of parameter values based on the calculated error metrics. In some instances, the error metrics are generated by calculating a sum-of-squared-errors, the first set of parameter values is associated with a smaller calculated error metric than the third set of parameter values, and the second set of parameter values is associated with a smaller calculated error metric than the fourth set of parameter values.

In one embodiment, the method includes receiving a series of uncompensated analyte measurements, deriving a first set of weighting coefficients from the first set of parameter values, deriving a third set of weighting coefficients from the third set of parameter values; and calculating lag-compensated point measurements by averaging a first output and a third output. The first output is generated by applying the first set of weighting coefficients to corresponding uncompensated analyte measurements received at the initial reference time, at the first prior reference time, and at the second prior reference time of the first set of parameter values. The third output is generated by applying the third set of weighting coefficients to corresponding uncompensated analyte measurements received at the initial reference time, at the first prior reference time, and at the second prior reference time of the third set of parameter values. The method further includes deriving a second set of weighting coefficients from the second set of parameter values, deriving a fourth set of weighting coefficients from the fourth set of parameter values, and calculating lag-compensated rate-of-change measurements by averaging a second output and a fourth output. The second output is generated by applying the second set of weighting coefficients to corresponding uncompensated analyte measurements received at the initial reference time, at the third prior reference time, and at the fourth prior reference time of the second set of parameter values. The fourth output is generated by applying the fourth set of weighting coefficients to corresponding uncompensated analyte measurements received at the initial reference time, at the third prior reference time, and at the fourth prior reference time of the fourth set of parameter values.

In one embodiment, the method includes receiving a series of uncompensated analyte measurements, deriving a first set of weighting coefficients from the first set of parameter values, and deriving a third set of weighting coefficients from the third set of parameter values. When valid data is present at the first prior reference time and the second prior reference time of the first set of parameter values, lag-compensated point measurements are calculated from the uncompensated analyte measurements by applying the first set of weighting coefficients to corresponding uncompensated analyte measurements received at the initial reference time, at the first prior reference time, and at the second prior reference time of the first set of parameter values. When valid data is present at the first prior reference time and the second prior reference time of the second set of parameter values and not the first set of parameter values, lag-compensated point measurements are calculated from the uncompensated analyte measurements by applying the third set of weighting coefficients to corresponding uncompensated analyte measurements received at the initial reference time, at the first prior reference time, and at the second prior reference time of the third set of parameter values. The method further includes deriving a second set of weighting coefficients from the second set of parameter values, and deriving a fourth set of weighting coefficients from the fourth set of parameter values. When valid data is present at the third prior reference time and the fourth prior reference time of the second set of parameter values, lag-compensated rate-of-change measurements are calculated from the uncompensated analyte measurements by applying the second set of weighting coefficients to corresponding uncompensated analyte measurements received at the initial reference time, at the third prior reference time, and at the fourth prior reference time for the second set of parameter values. When valid data is present at the third prior reference time and the fourth prior reference time for the fourth set of parameter values and not the second set of parameter values, lag-compensated rate-of-change measurements are calculated from the uncompensated analyte measurements by applying the fourth set of weighting coefficients to corresponding uncompensated analyte measurements received at the initial reference time, at the third prior reference time, and at the fourth prior reference time of the fourth set of parameter values.

In some embodiments, a third filter is implemented. In one embodiment, the method includes determining a fifth set of parameter values for the analyte point estimate based on the reference analyte measurements. The first set, the third set, and the fifth set of parameter values point to different sets of prior reference times. The method further includes determining a sixth set of parameter values for the analyte rate-of-change estimate based on the reference analyte measurements. The second set, the fourth set, and the sixth set of parameter values point to different sets of prior reference times.

In one embodiment, the determining of the first set, second set, third set, fourth set, fifth set, and sixth set of parameter values includes calculating error metrics for a plurality of combinations of values as parameters in the analyte point estimates and the analyte rate-of-change estimates, and selecting the first set, second set, third set, fourth set, fifth set, and sixth set of parameter values based on the calculated error metrics. In some instances, the error metrics are generated by calculating a sum-of-squared-errors, the first set of parameter values is associated with a smaller calculated error metric than the third set of parameter values, the third set of parameter values is associated with a smaller calculated error metric than the fifth set of parameter values, the second set of parameter values is associated with a smaller calculated error metric than the fourth set of parameter values, and the fourth set of parameter values is associated with a smaller calculated error metric than the sixth set of parameter values.

In one embodiment, the method includes receiving a series of uncompensated analyte measurements; deriving a first set of weighting coefficients from the first set of parameter values; deriving a third set of weighting coefficients from the third set of parameter values; deriving a fifth set of weighting coefficients from the fifth set of parameter values; calculating lag-compensated point measurements by averaging available outputs, wherein the available outputs are generated by applying the first, third, and/or fifth sets of weighting coefficients to uncompensated analyte measurements received at the initial reference time, the first prior reference time, and the second prior reference time of respective first, third, and/or fifth sets of parameter values which have valid data present; deriving a second set of weighting coefficients from the second set of parameter values; deriving a fourth set of weighting coefficients from the fourth set of parameter values; deriving a sixth set of weighting coefficients from the sixth set of parameter values; and calculating lag-compensated rate-of-change measurements by averaging available outputs, wherein the available outputs are generated by applying the second, fourth, and/or sixth sets of weighting coefficients to uncompensated analyte measurements received at the initial reference time, the third prior reference time, and the fourth prior reference time of respective first, second, and/or third sets of parameter values which have valid data present.

In one embodiment, the method includes receiving a series of uncompensated analyte measurements, deriving a first set of weighting coefficients from the first set of parameter values, deriving a third set of weighting coefficients from the third set of parameter values, and deriving a fifth set of weighting coefficients from the fifth set of parameter values. When valid data is present at the first prior reference time and the second prior reference time of the first set of parameter values, lag-compensated point measurements are calculated from the uncompensated analyte measurements by applying the first set of weighting coefficients to corresponding uncompensated analyte measurements received at the initial reference time, at the first prior reference time, and at the second prior reference time of the first set of parameter values. When valid data is present at the first prior reference time and the second prior reference time of the third set of parameter values and not the first set of parameter values, lag-compensated point measurements are calculated from the uncompensated analyte measurements by applying the third set of weighting coefficients to corresponding uncompensated analyte measurements received at the initial reference time, at the first prior reference time, and at the second prior reference time of the third set of parameter values. When valid data is present at the first prior reference time and the second prior reference time of the fifth set of parameter values and not the first set or the third set of parameter values, lag-compensated point measurements are calculated from the uncompensated analyte measurements by applying the fifth set of weighting coefficients to corresponding uncompensated analyte measurements received at the initial reference time, at the first prior reference time, and at the second prior reference time of the fifth set of parameter values. The method further includes deriving a second set of weighting coefficients from the second set of parameter values, deriving a fourth set of weighting coefficients from the fourth set of parameter values, and deriving a sixth set of weighting coefficients from the fifth set of parameter values. When valid data is present at the third prior reference time and the fourth prior reference time of the second set of parameter values, lag-compensated rate-of-change measurements are calculated from the uncompensated analyte measurements by applying the second set of weighting coefficients to corresponding uncompensated analyte measurements received at the initial reference time, at the third prior reference time, and at the fourth prior reference time of the second set of parameter values. When valid data is present at the third prior reference time and the fourth prior reference time of the fourth set of parameter values and not the second set of parameter values, lag-compensated rate-of-change measurements are calculated from the uncompensated analyte measurements by applying the fourth set of weighting coefficients to corresponding uncompensated analyte measurements received at the initial reference time, at the third prior reference time, and at the fourth prior reference time of the fourth set of parameter values. When valid data is present at the third prior reference time and the fourth prior reference time of the sixth set of parameter values and not the second set or the fourth set of parameter values, lag-compensated rate-of-change measurements are calculated from the uncompensated analyte measurements by applying the sixth set of weighting coefficients to corresponding uncompensated analyte measurements received at the initial reference time, at the third prior reference time, and at the fourth prior reference time of the sixth set of parameter values.

In some embodiments, four or more filters are implemented. In one embodiment, the method includes determining three or more additional sets of parameter values for the analyte point estimate based on the reference analyte measurements, wherein the three or more additional sets of parameter values point to different sets of prior reference times; and/or determining three or more additional sets of parameter values for the analyte rate-of-change estimate based on the reference analyte measurements, wherein the three or more additional sets of parameter values point to different sets of prior reference times.

In some embodiments, a second bank of an analyte point estimate is implemented. In one embodiment, the method includes determining a seventh set of parameter values for a second analyte point estimate. The second analyte point estimate is based on a sum of an analyte point and a sum of a third plurality of scaled rates-of-changes. The analyte point corresponds to measurements at an first alternate initial reference time, wherein the first alternate initial reference time is prior to the initial reference time by a first time delay. The rates-of-changes of the third plurality include a fifth rate-of-change from the first alternate initial reference time to a fifth prior reference time with respect to the first alternate initial reference time, and a sixth rate-of-change from the first alternate initial reference time to a sixth prior reference time with respect to the first alternate initial reference time.

In one embodiment, the method includes deriving a first set of weighting coefficients from the first set of parameter values; calculating first lag-compensated point measurements from the uncompensated analyte measurements by applying the first set of weighting coefficients to corresponding uncompensated analyte measurements received at the initial reference time, at the first prior reference time, and at the second prior reference time of the first set of parameter values; deriving a seventh set of weighting coefficients from the seventh set of parameter values; calculating second lag-compensated point measurements from the uncompensated analyte measurements by applying the seventh set of weighting coefficients to corresponding uncompensated analyte measurements received at the first alternate initial reference time, at the fifth prior reference time, and at the sixth prior reference time of the seventh set of parameter values; determining a severity of discrepancy between the first and the second analyte point estimates; and generating resulting lag-compensated point measurements based on a weighted sum of the first lag compensated output and the second lag-compensated output, wherein the weighted sum is based on the severity of discrepancy.

In some embodiments, a second bank of analyte rate-of-change estimate is implemented. In one embodiment, the method includes determining an eighth set of parameter values for a second analyte rate-of-change estimate. The second analyte rate-of-change estimate is based on a sum of a fourth plurality of scaled rates-of-changes. The rates-of-changes of the fourth plurality include a seventh rate-of-change from a second alternate initial reference time to an seventh prior reference time with respect to the second alternate initial reference time, and an eighth rate-of-change from the second alternate initial reference time to an eighth prior reference time with respect to the second alternate initial reference time. The second alternate initial reference time is prior to the initial reference time by a second time delay.

In one embodiment, the method includes deriving a second set of weighting coefficients from the second set of parameter values; calculating first lag-compensated rate-of-change measurements from the uncompensated analyte measurements by applying the second set of weighting coefficients to corresponding uncompensated analyte measurements received at the initial reference time, at the third prior reference time, and at the fourth prior reference time of the second set of parameter values; deriving an eighth set of weighting coefficients from the eighth set of parameter values; calculating second lag-compensated rate-of-change measurements from the uncompensated analyte measurements by applying the eighth set of weighting coefficients to corresponding uncompensated analyte measurements received at the second alternate initial reference time, at the seventh prior reference time, and at the eighth prior reference time of the eighth set of parameter values; determining a severity of discrepancy between the first and the second analyte rate-of-change estimates; and generating resulting lag-compensated rate-of-change measurements based on a weighted sum of the first lag compensated rate-of-change measurements and the second lag-compensated rate-of-change measurements, wherein the weighting is based on the severity of discrepancy.

In some instances, the first time delay and/or second time delay is predetermined based on a projected size of artifacts.

In some embodiments, the analyte point estimate includes three or more rates-of-changes.

In one embodiment, the rates-of-changes of the first plurality include one or more additional rates-of-changes from the initial reference time to additional prior reference times.

In one embodiment, the method includes receiving a series of uncompensated analyte measurements, deriving weighting coefficients from the first set of parameter values, and calculating lag-compensated point measurements from the uncompensated analyte measurements. The lag-compensated point measurements are calculated by applying the weighting coefficients to corresponding uncompensated analyte measurements received at the initial reference time, at the first prior reference time, at the second prior reference time, and at each of the additional prior reference times.

In some embodiments, the analyte rate-of-change estimate includes three or more rates-of-changes. In one embodiment, the rates-of-changes of the second plurality include one or more additional rates-of-changes from the initial reference time to additional prior reference times.

In one embodiment, the method includes receiving a series of uncompensated analyte measurements, deriving weighting coefficients from the second set of parameter values, and calculating lag-compensated rate-of-change measurements from the uncompensated analyte measurements. The lag-compensated rate-of-change measurements are calculated by applying the weighting coefficients to corresponding uncompensated analyte measurements received at the initial reference time, at the third prior reference time, at the fourth prior reference time, and at each of the additional prior reference times.

As stated above, in some aspects of the present disclosure, articles of manufacture for lag compensation of analyte point measurements and analyte rate-of-change measurements are provided. The articles of manufacture include a machine-readable medium having machine-executable instructions stored thereon for lag compensation of analyte measurements. The instructions include instructions for receiving reference analyte measurements, and instructions for determining a first set of parameter values for an analyte point estimate based on the reference analyte measurements. The analyte point estimate is based on a sum of an analyte point and a sum of a first plurality of scaled rates-of-changes. The analyte point corresponds to measurements at an initial reference time. The rates-of-changes of the first plurality include a first rate-of-change from the initial reference time to a first prior reference time and a second rate-of-change from the initial reference time to a second prior reference time. The articles of manufacture also include instructions for determining a second set of parameter values for an analyte rate-of-change estimate based on the reference analyte measurements. The analyte rate-of-change estimate is based on the sum of a second plurality of scaled rates-of-changes. The rates-of-changes of the second plurality include a third rate-of-change from an initial reference time to a third prior reference time, and a fourth rate-of-change from the initial reference time to a fourth prior reference time.

It should be appreciated that similar embodiments to those described above for the methods of lag compensation for analyte point measurements and analyte rate-of-change measurements are applicable to articles of manufacture as well.

It should be understood that techniques introduced above can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

Furthermore, a data processing device or system, such as a computer or computer system may be configured to execute some of the techniques introduced herein. The computer may include, for example, a processing device, memory with instructions stored therein to perform the techniques, input/output device elements (e.g., a monitor, keyboard, etc.), etc. For example, the device or system may be used to configure, calibrate, or otherwise program an analyte monitoring device intended to perform analyte measurements, such as analyte point measurements and/or analyte rate-of-change measurements. In some aspects of the present disclosure, some of the techniques described herein may be provided to the device or system from an article of manufacture including the machine readable medium described above.

The preceding examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

That which is claimed is:

1. A method of determining glucose level in a subject, comprising:
    inserting an in vivo sensor in subcutaneous tissue in contact with interstitial fluid of a subject;
    positioning an on-body unit on a surface of skin of the subject, wherein the on-body unit is in electrical contact with the in vivo sensor and in communication with a display;
    measuring glucose in the interstitial fluid of the subject with the in vivo glucose sensor to produce at least three uncompensated glucose measurements, wherein the three uncompensated glucose measurements including a first uncompensated glucose measurement at an initial reference time, a second uncompensated glucose measurement at a first prior reference time, and a third uncompensated glucose measurement at a second prior reference time;
    determining a first scaled rate-of-change by multiplying a first weighting coefficient on a first rate of change computed from the first uncompensated glucose measurement at the initial reference time relative to the second uncompensated glucose measurement at the first prior reference time;
    determining a second scaled rate-of-change by multiplying a second weighting coefficient on a second rate of change computed from the first uncompensated glucose measurement at the initial reference time relative to the second uncompensated glucose measurement at the second prior reference time; and
    calculating a lag-compensated glucose level from the uncompensated glucose measurements by adding the first scaled rate-of-change, the second scaled rate-of-change and the first uncompensated glucose measurement; and displaying the lag compensated glucose level to the subject on the display, wherein the lag-compensated glucose level correlates with the subject's blood glucose level at the initial reference time.

2. The method of claim 1, further comprising determining a first set of parameter values for a glucose level estimate based on the at least three glucose measurements, wherein the glucose level estimate is based on a sum of:
a glucose level corresponding to measurements at an initial reference time; and
a sum of the first scaled rate-of-change and the second scaled rate-of-change.

3. The method of claim 2, wherein the first set of parameter values comprises:
a first weighting coefficient of the first rate-of-change;
the first prior reference time;
a second weighting coefficient of the second rate-of-change; and
the second prior reference time.

4. A device, comprising:
an in vivo positionable glucose sensor;
a processor,
a display for communicating lag compensated glucose level, wherein the lag compensated glucose level correlates with the subject's blood glucose level at an initial reference time and
a memory comprising machine-executable instructions stored thereon for lag compensation of glucose level measurements, the instructions when executed cause the processor to:
receive at least three uncompensated glucose measurements prior to lag compensation, wherein the three uncompensated glucose measurements including a first uncompensated glucose measurement at the initial reference time, a second uncompensated glucose measurement at a first prior reference time, and a third uncompensated glucose measurement at a second prior reference time; and
determine a first scaled rate-of-change by multiplying a first weighting coefficient on a first rate of change computed from the first uncompensated glucose measurement at the initial reference time to the second uncompensated glucose measurement at the first prior reference time and determine a second scaled rate-of-change by multiplying a second weight coefficient on a second rate of change computed from the first uncompensated glucose measurement at the initial reference time to the second uncompensated glucose measurement at the second prior reference time; and
calculate lag-compensated glucose level measurements from the uncompensated glucose measurements by adding the first scaled rate-of-change, the second scaled rate-of-change and the first uncompensated glucose measurement.

5. The device of claim 4, the instructions when executed cause the processor to determine a first set of parameter values for a glucose level estimate based on at least three glucose measurements, wherein the glucose level estimate is based on a sum of:
a glucose level corresponding to measurements at an initial reference time; and
a sum of the first scaled rate-of-change and the second scaled rate-of-change.

6. The device of claim 5, where the instructions comprise:
instructions for calculating error metrics for a plurality of combinations of values as parameters in the glucose level estimate; and
instructions for selecting the first set of parameter values based on the calculated error metrics.

7. The method of claim 1, further comprising measuring glucose in the interstitial fluid of the subject with the in vivo glucose sensor to produce a fourth uncompensated glucose measurement at a third prior reference time and a fifth uncompensated measurement at a fourth prior reference time.

8. The method of claim 7, further comprising:
determining a third scaled rate of change by multiplying a third weighting coefficient on a third rate of change computed from the first uncompensated glucose measurement at the initial reference time relative to the fourth uncompensated glucose measurement at the third prior reference time; and
determining a fourth scaled rate of change by multiplying a fourth weighting coefficient on a fourth rate of change computed from the first uncompensated glucose measurement at the initial reference time relative to the fifth uncompensated glucose measurement at the fourth prior reference time.

9. The method of claim 8, further comprising calculating a lag-compensated glucose level from the uncompensated glucose measurements by adding the first uncompensated glucose measurement with the third scaled rate-of-change and the fourth scaled rate-of-change.

10. The method of claim 9, wherein a second set of parameter values comprises:
a third weighting coefficient of the third rate-of-change;
the third prior reference time;
a fourth weighting coefficient of the fourth rate-of-change;
the fourth prior reference time.

11. The method of claim 9, further comprising calculating a lag-compensated glucose level by averaging a first lag-compensated glucose level and a second lag-compensated glucose level; where the first lag-compensated glucose level is the sum of the first uncompensated glucose measurement, the first scaled rate-of-change, and the second scaled rate-of-change; and where the second lag-compensated glucose level is the sum of the first uncompensated glucose measurement, the third scaled rate-of-change, and the fourth scaled rate-of-change.

12. The method of claim 7, further comprising measuring glucose in the interstitial fluid of the subject with the in vivo glucose sensor to produce a sixth uncompensated glucose measurement at a fifth prior reference time and a seventh uncompensated measurement at a sixth prior reference time.

13. The method of claim 12, further comprising:
determining a fifth scaled rate of change by multiplying a fifth weighting coefficient on a fifth rate of change computed from the first uncompensated glucose measurement at the initial reference time relative to the sixth uncompensated glucose measurement at the fifth prior reference time; and
determining a sixth scaled rate of change by multiplying a sixth weighting coefficient on a sixth rate of change computed from the first uncompensated glucose measurement at the initial reference time relative to the seventh uncompensated glucose measurement at the sixth prior reference time.

14. The method of claim 12, further comprising calculating a lag-compensated glucose level from the uncompensated glucose measurements by adding the first uncompensated glucose measurement with the fifth scaled rate of change and the sixth scaled rate of change.

15. The method of claim 14, wherein a third set of parameter values comprises:
a fifth weighting coefficient of the fifth rate-of-change;
the fifth prior reference time;
a sixth weighting coefficient of the sixth rate-of-change;
the sixth prior reference time.

16. The method of claim 12, further comprising calculating a lag-compensated glucose level by averaging a first lag-compensated glucose level and a second lag-compensated glucose level and a third lag-compensated glucose level; where the first lag-compensated glucose level is the sum of the first uncompensated glucose measurement, the first scaled rate-of-change, and the second scaled rate-of-change; the second lag-compensated glucose level is the sum of the first uncompensated glucose measurement, the third scaled rate-of-change, and the fourth scaled rate-of-change; the third lag-compensated glucose level is the sum of the first uncompensated glucose measurement, the fifth scaled rate of change, and the sixth scaled rate of change.

17. The method of claim 16, further comprising determining whether one or more of the uncompensated glucose measurements are physiologically infeasible, invalid or missing.

18. The method of claim 17, wherein when the second uncompensated glucose measurement or the third uncompensated glucose measurement is determined to be physiologically infeasible, invalid or missing, the method comprises:
calculating a lag-compensated glucose level by adding the first uncompensated glucose measurement with:
the third scaled rate-of-change and the fourth scaled rate-of-change; or
the fifth scaled rate-of-change and the sixth scaled rate-of-change.

19. The method of claim 18, wherein the method comprises calculating a lag-compensated glucose level by adding the first uncompensated glucose measurement with the third scaled rate-of-change and the fourth scaled rate-of-change.

20. The method of claim 18, wherein the method comprises calculating a lag-compensated glucose level by adding the first uncompensated glucose measurement with the fifth scaled rate-of-change and the sixth scaled rate-of-change.

21. The method of claim 17, wherein when the fourth uncompensated glucose measurement or the fifth uncompensated glucose measurement is determined to be physiologically infeasible, invalid or missing, the method comprises:
calculating a lag-compensated glucose level by adding the first uncompensated glucose measurement with:
the first scaled rate-of-change and the second scaled rate-of-change; or
the fifth scaled rate-of-change and the sixth scaled rate-of-change.

22. The method of claim 21, wherein the method comprises calculating a lag-compensated glucose level by adding the first uncompensated glucose measurement with the first scaled rate-of-change and the second scaled rate-of-change.

23. The method of claim 21, wherein the method comprises calculating a lag-compensated glucose level by adding the first uncompensated glucose measurement with the fifth scaled rate-of-change and the sixth scaled rate-of-change.

24. The method of claim 17, wherein when the sixth uncompensated glucose measurement or the seventh uncompensated glucose measurement is determined to be physiologically infeasible, invalid or missing, the method comprises:
calculating a lag-compensated glucose level by adding the first uncompensated glucose measurement with:
the first scaled rate-of-change and the second scaled rate-of-change; or
the third scaled rate-of-change and the fourth scaled rate-of-change.

25. The method of claim 24, wherein the method comprises calculating a lag-compensated glucose level by adding the first uncompensated glucose measurement with the first scaled rate-of-change and the second scaled rate-of-change.

26. The method of claim 24, wherein the method comprises calculating a lag-compensated glucose level by adding the first uncompensated glucose measurement with the third scaled rate-of-change and the fourth scaled rate-of-change.

27. The method of claim 16, further comprising determining whether one or more the first rate-of-change, the second rate-of-change, the third rate-of-change, the fourth rate-of-change the fifth rate of change and the sixth rate of change are physiologically infeasible.

28. The method of claim 17, wherein the physiologically infeasible rate of change is indicative of a dropout.

29. The method of claim 1, comprising determining an alternate first uncompensated glucose measurement at an alternate initial reference time.

30. The method of claim 29, wherein the alternate initial reference time is offset with respect to the initial reference time by a time delay.

31. The method of claim 30, further comprising determining an alternate first scaled rate-of-change by multiplying the alternate first weighting coefficient on an alternate first rate of change computed from the alternate first uncompensated glucose measurement at the alternate initial reference time to the alternate second uncompensated glucose measurement at the alternate first prior reference time.

32. The method of claim 31, further comprising determining an alternate second scaled rate-of-change by multiplying the alternate second weighting coefficient on an alternate second rate of change computed from the alternate first uncompensated glucose measurement at the alternate initial reference time to the alternate third uncompensated glucose measurement at the alternate second prior reference time.

33. The method of claim 32, further comprising calculating an alternate lag compensated glucose level from the uncompensated glucose measurements by adding the alternate first uncompensated glucose measurement, the alternate first scaled rate-of-change and the alternate second scaled rate-of-change.

34. The method of claim 31, further comprising determining:
an alternate third scaled rate-of-change by multiplying an alternate third weighting coefficient on an alternate third rate of change computed from the alternate first uncompensated glucose measurement at the alternate initial reference time to an alternate fourth uncompensated glucose measurement at an alternate third prior reference time; and
an alternate fourth scaled rate-of-change by multiplying an alternate fourth weighting coefficient on an alternate fourth rate of change computed from the alternate first uncompensated glucose measurement at the alternate initial reference time to an alternate fifth uncompensated glucose measurement at an alternate fourth prior reference time.

35. The method of claim 34, further comprising calculating an alternate lag-compensated glucose level by averaging an alternate first lag-compensated glucose level and an alternate second lag-compensated glucose level; where the alternate first lag-compensated glucose level is the sum of the alternate first uncompensated glucose measurement, the alternate first scaled rate-of-change, and the alternate second scaled rate-of-change; and where the alternate second lag-compensated glucose level is the sum of the alternate first uncompensated glucose measurement, the alternate third scaled rate-of-change and the alternate fourth scaled rate-of-change.

36. The device of claim 4, wherein the memory further comprises instructions when executed cause the processor to receive a fourth uncompensated glucose measurement at a third prior reference time and a fifth uncompensated measurement at a fourth prior reference time.

37. The device of claim 36, wherein the memory further comprises instructions when executed cause the processor to:
determine a third scaled rate of change by multiplying a third weighting coefficient on a third rate of change computed from the first uncompensated glucose measurement at the initial reference time relative to the fourth uncompensated glucose measurement at the third prior reference time; and
determine a fourth scaled rate of change by multiplying a fourth weighting coefficient on a fourth rate of change computed from the first uncompensated glucose measurement at the initial reference time relative to the fifth uncompensated glucose measurement at the fourth prior reference time.

38. The device of claim 37, wherein the memory further comprises instructions when executed cause the processor to calculate a lag-compensated glucose level from the uncompensated glucose measurements by adding the first uncompensated glucose measurement with the third scaled rate-of-change and the fourth scaled rate-of-change.

39. The device of claim 38, wherein the memory further comprises instructions when executed cause the processor to calculate a lag-compensated glucose level by averaging a first lag-compensated glucose level and a second lag-compensated glucose level; where the first lag-compensated glucose level is the sum of the first uncompensated glucose measurement, the first scaled rate-of-change, and the second scaled rate-of-change; and where the second lag-compensated glucose level is the sum of the first uncompensated glucose measurement, the third scaled rate-of-change, and the fourth scaled rate-of-change.

40. The device of claim 37, wherein the memory further comprises instructions when executed cause the processor to receive a sixth uncompensated glucose measurement at a fifth prior reference time and a seventh uncompensated measurement at a sixth prior reference time.

41. The device of claim 40, wherein the memory further comprises instructions when executed cause the processor to:
determine a fifth scaled rate of change by multiplying a fifth weighting coefficient on a fifth rate of change computed from the first uncompensated glucose measurement at the initial reference time relative to the sixth uncompensated glucose measurement at the fifth prior reference time; and determine a sixth scaled rate of change by multiplying a sixth weighting coefficient on a sixth rate of change computed from the first uncompensated glucose measurement at the initial reference time relative to the seventh uncompensated glucose measurement at the sixth prior reference time.

42. The device of claim 40, wherein the memory further comprises instructions when executed cause the processor to calculate a lag-compensated glucose level from the uncompensated glucose measurements by adding the first uncompensated glucose measurement with the fifth scaled rate of change and the sixth scaled rate of change.

43. The device of claim 40, wherein the memory further comprises instructions when executed cause the processor to calculate a lag-compensated glucose level by averaging a first lag-compensated glucose level and a second lag-compensated glucose level and a third lag-compensated glucose level; where the first lag-compensated glucose level is the sum of the first uncompensated glucose measurement, the first scaled rate-of-change, and the second scaled rate-of-change; the second lag-compensated glucose level is the sum of the first uncompensated glucose measurement, the third scaled rate-of-change, and the fourth scaled rate-of-change; the third lag-compensated glucose level is the sum of the first uncompensated glucose measurement, the fifth scaled rate of change, and the sixth scaled rate of change.

44. The device of claim 43, wherein the memory further comprises instructions when executed cause the processor to determine whether one or more of the uncompensated glucose measurements are physiologically infeasible, invalid or missing.

45. The device of claim 44, wherein when the second uncompensated glucose measurement or the third uncompensated glucose measurement is determined to be physiologically infeasible, invalid or missing, the memory further comprises instructions when executed cause the processor to:
calculate a lag-compensated glucose level by adding the first uncompensated glucose measurement with:
the third scaled rate-of-change and the fourth scaled rate-of-change; or
the fifth scaled rate-of-change and the sixth scaled rate-of-change.

46. The device of claim 45, wherein the memory further comprises instructions when executed cause the processor to calculate a lag-compensated glucose level by adding the first uncompensated glucose measurement with the third scaled rate-of-change and the fourth scaled rate-of-change.

47. The device of claim 45, wherein the memory further comprises instructions when executed cause the processor to calculate a lag-compensated glucose level by adding the first uncompensated glucose measurement with the fifth scaled rate-of-change and the sixth scaled rate-of-change.

48. The device of claim 44, wherein when the fourth uncompensated glucose measurement or the fifth uncompensated glucose measurement is determined to be physiologically infeasible, invalid or missing, the memory further comprises instructions when executed cause the processor to:
calculate a lag-compensated glucose level by adding the first uncompensated glucose measurement with:
the first scaled rate-of-change and the second scaled rate-of-change; or
the fifth scaled rate-of-change and the sixth scaled rate-of-change.

49. The device of claim 48, wherein the memory further comprises instructions when executed cause the processor to calculate a lag-compensated glucose level by adding the first uncompensated glucose measurement with the first scaled rate-of-change and the second scaled rate-of-change.

50. The device of claim 48, wherein the memory further comprises instructions when executed cause the processor to calculate a lag-compensated glucose level by adding the first uncompensated glucose measurement with the fifth scaled rate-of-change and the sixth scaled rate-of-change.

51. The device of claim 44, wherein when the sixth uncompensated glucose measurement or the seventh uncompensated glucose measurement is determined to be physiologically infeasible, invalid or missing, the memory further comprises instructions when executed cause the processor to:
calculate a lag-compensated glucose level by adding the first uncompensated glucose measurement with:
the first scaled rate-of-change and the second scaled rate-of-change; or
the third scaled rate-of-change and the fourth scaled rate-of-change.

52. The device of claim 51, wherein the memory further comprises instructions when executed cause the processor to calculate a lag-compensated glucose level by adding the first uncompensated glucose measurement with the first scaled rate-of-change and the second scaled rate-of-change.

53. The device of claim 51, wherein the memory further comprises instructions when executed cause the processor to calculate a lag-compensated glucose level by adding the first uncompensated glucose measurement with the third scaled rate-of-change and the fourth scaled rate-of-change.

54. The device of claim 44, wherein the memory further comprises instructions when executed cause the processor to determine whether one or more the first rate-of-change, the second rate-of-change, the third rate-of-change, the fourth rate-of-change the fifth rate of change and the sixth rate of change are physiologically infeasible.

55. The device of claim 44, wherein the physiologically infeasible rate of change is indicative of a dropout.

56. The device of claim 4, wherein the memory further comprises instructions when executed cause the processor to determine an alternate first uncompensated glucose measurement at an alternate initial reference time.

57. The device of claim 56, wherein the alternate initial reference time is offset with respect to the initial reference time by a time delay.

58. The device of claim 57, wherein the memory further comprises instructions when executed cause the processor to determine an alternate first scaled rate-of-change by multiplying the alternate first weighting coefficient on an alternate first rate of change computed from the alternate first uncompensated glucose measurement at the alternate initial reference time to the alternate second uncompensated glucose measurement at the alternate first prior reference time.

59. The device of claim 58, wherein the memory further comprises instructions when executed cause the processor to determine an alternate second scaled rate-of-change by multiplying the alternate second weighting coefficient on an alternate second rate of change computed from the alternate first uncompensated glucose measurement at the alternate initial reference time to the alternate third uncompensated glucose measurement at the alternate second prior reference time.

60. The device of claim 59, wherein the memory further comprises instructions when executed cause the processor to calculate an alternate lag compensated glucose level from the uncompensated glucose measurements by adding the alternate first uncompensated glucose measurement, the alternate first scaled rate-of-change and the alternate second scaled rate-of-change.

61. The device of claim 58, wherein the memory further comprises instructions when executed cause the processor to determine:
an alternate third scaled rate-of-change by multiplying an alternate third weighting coefficient on an alternate third rate of change computed from the alternate first uncompensated glucose measurement at the alternate initial reference time to an alternate fourth uncompensated glucose measurement at an alternate third prior reference time; and
an alternate fourth scaled rate-of-change by multiplying an alternate fourth weighting coefficient on an alternate fourth rate of change computed from the alternate first uncompensated glucose measurement at the alternate initial reference time to an alternate fifth uncompensated glucose measurement at an alternate fourth prior reference time.

62. The device of claim 61, wherein the memory further comprises instructions when executed cause the processor to calculate an alternate lag-compensated glucose level by averaging an alternate first lag-compensated glucose level and an alternate second lag-compensated glucose level; where the alternate first lag-compensated glucose level is the sum of the alternate first uncompensated glucose measurement, the alternate first scaled rate-of-change, and the alternate second scaled rate-of-change; and where the alternate second lag-compensated glucose level is the sum of the alternate first uncompensated glucose measurement, the alternate third scaled rate-of-change and the alternate fourth scaled rate-of-change.

\* \* \* \* \*